US012667520B2

(12) United States Patent
Marcantonio et al.

(10) Patent No.: US 12,667,520 B2
(45) Date of Patent: Jun. 30, 2026

(54) ACUPUNCTURE DEVICE AND METHOD OF USING MAGNETIC FIELDS TO STIMULATE ACUPUNCTURE NEEDLES, AND MAGNETIC COIL CONFIGURATIONS

(71) Applicants: Dennis Marcantonio, Palm Beach Gardens, FL (US); Greg Bartosiewicz, Jupiter, FL (US)

(72) Inventors: Dennis Marcantonio, Palm Beach Gardens, FL (US); Greg Bartosiewicz, Jupiter, FL (US)

( * ) Notice: Subject to any disclaimer, the term of this patent is extended or adjusted under 35 U.S.C. 154(b) by 1085 days.

(21) Appl. No.: 17/663,063

(22) Filed: May 12, 2022

(65) Prior Publication Data

US 2022/0265511 A1 Aug. 25, 2022

Related U.S. Application Data

(63) Continuation-in-part of application No. 16/585,080, filed on Sep. 27, 2019, now Pat. No. 11,344,738.
(Continued)

(51) Int. Cl.
*A61H 39/08* (2006.01)
*A61N 2/02* (2006.01)
(Continued)

(52) U.S. Cl.
CPC .............. *A61H 39/086* (2013.01); *A61N 2/02* (2013.01); *H01F 27/2823* (2013.01); *A61H 2039/005* (2013.01)

(58) Field of Classification Search
CPC .......... A61N 2/00; A61N 2/002; A61N 2/004; A61N 2/006; A61N 2/008; A61N 2/02;
(Continued)

(56) References Cited

U.S. PATENT DOCUMENTS 5,116,304 A * 5/1992 Cadwell ................... A61N 2/02
600/15
6,858,036 B1 2/2005 Kim
(Continued)

FOREIGN PATENT DOCUMENTS

RU 2195329 12/2002

*Primary Examiner* — Carrie R Dorna
(74) *Attorney, Agent, or Firm* — McHale & Slavin, P.A.

(57) ABSTRACT

Devices and methods for generating and applying stimulated acupuncture needles to one or more acupuncture points on a body of an individual suffering from one or more ailments using magnetic fields. The acupuncture device is configured for generating magnetic fields to stimulate acupuncture without using human manual manipulation. The acupuncture device may comprise a control unit and one or more acupuncture needle stimulation units. Each one or more acupuncture needle stimulation unit is functionally connected to the control unit by a cable or lead. The control unit may include a variable frequency generator configured to deliver various power levels, direct voltages, or a combination of various power levels and direct voltages to the acupuncture needle stimulation units, alone or in combination with other stimuli. Special magnetic coil configurations may be used to boost coil efficiently and reduce the required energy to generate comparable magnetic fields.

9 Claims, 18 Drawing Sheets

Related U.S. Application Data

(60) Provisional application No. 62/738,111, filed on Sep. 28, 2018.

(51) Int. Cl.
 *H01F 27/28* (2006.01)
 *A61H 39/00* (2006.01)

(58) Field of Classification Search
 CPC .. A61H 39/08; A61H 39/086; H01F 27/2823;
 H01F 27/2828; H01F 5/02; H01F 5/04;
 H01F 2005/006
 See application file for complete search history.

(56) References Cited

U.S. PATENT DOCUMENTS

| | | |
|---|---|---|
| 8,226,540 B1 | 7/2012 | Chi |
| 2007/0208404 A1 | 9/2007 | Jones et al. |
| 2009/0108969 A1* | 4/2009 | Sims ...................... H01F 27/18 |
| | | 335/300 |
| 2010/0152763 A1 | 6/2010 | Kim et al. |
| 2014/0135875 A1 | 5/2014 | Kim et al. |
| 2015/0306386 A1 | 10/2015 | Alpert et al. |
| 2020/0101307 A1 | 4/2020 | Marcantonio et al. |

* cited by examiner

10
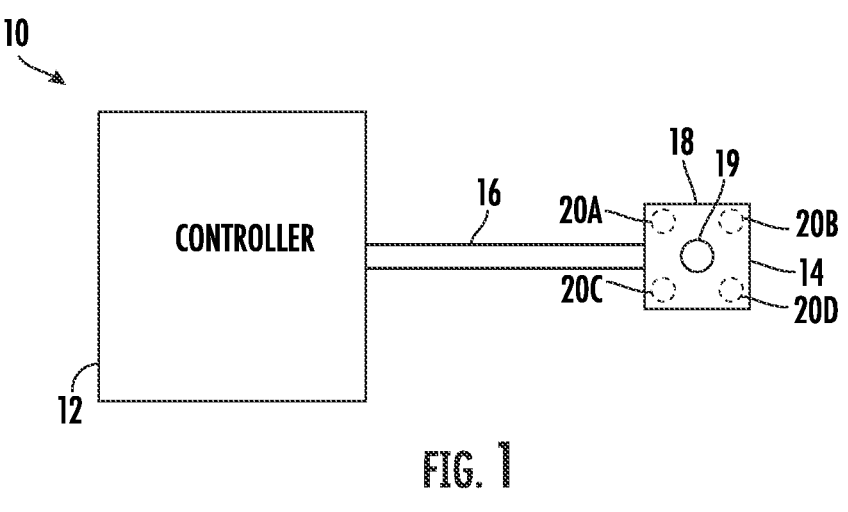
FIG. 1
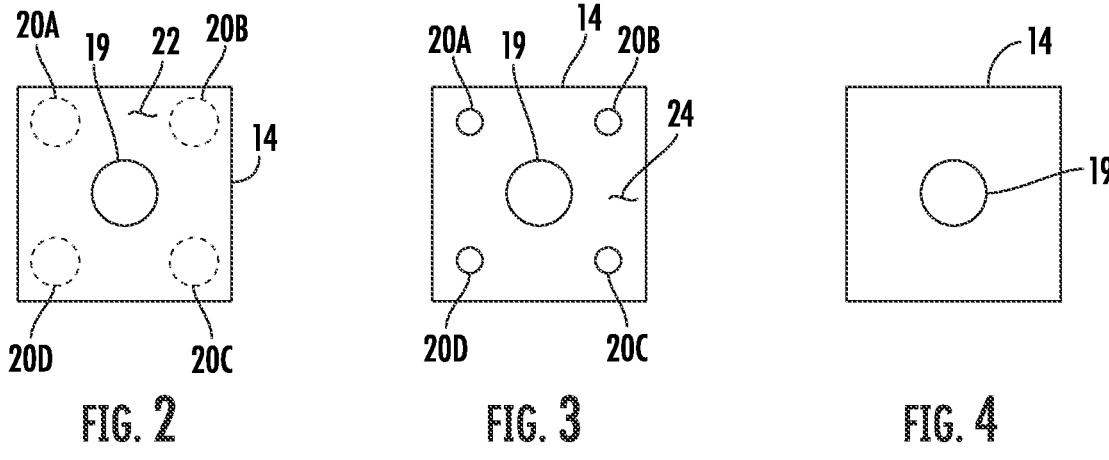
FIG. 2                        FIG. 3                        FIG. 4
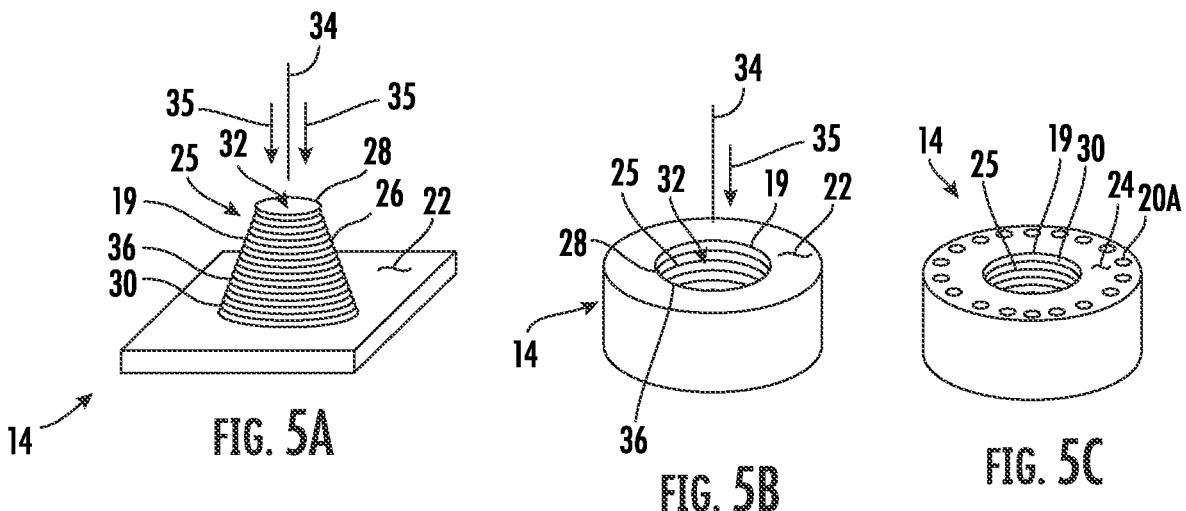
FIG. 5A                FIG. 5B                FIG. 5C

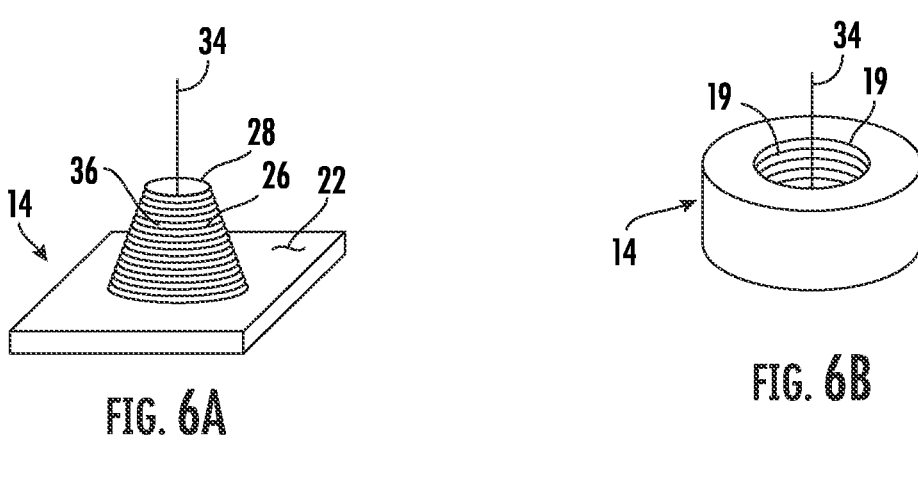
FIG. 6A
FIG. 6B
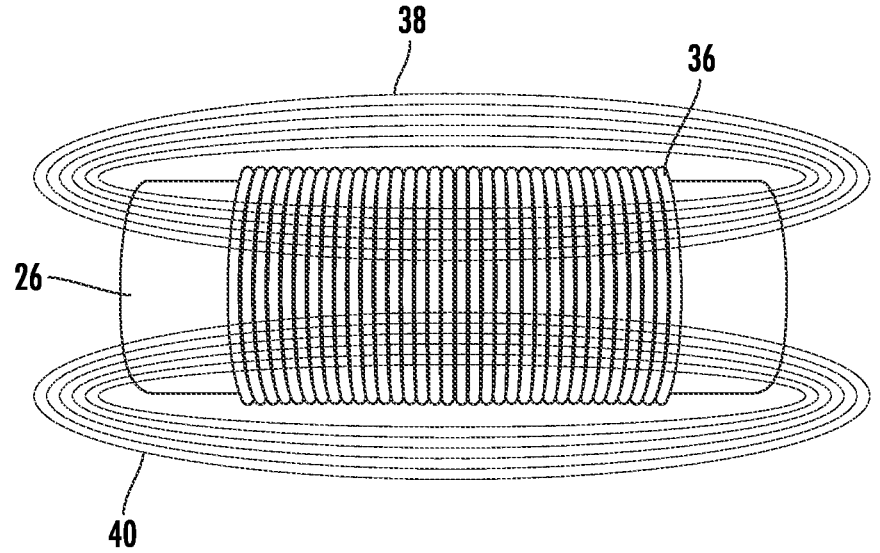
FIG. 7
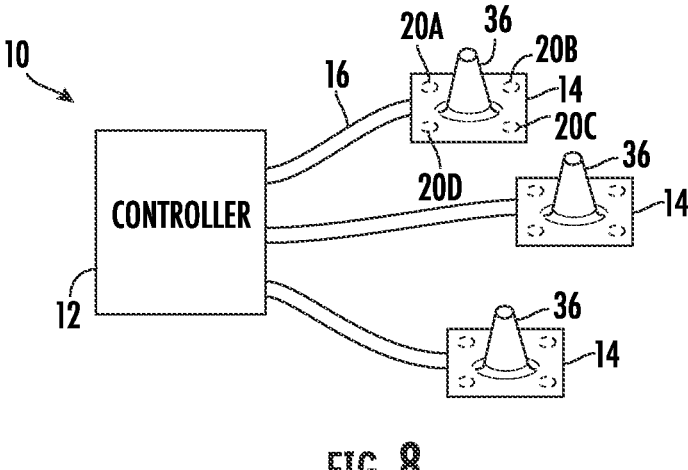
FIG. 8

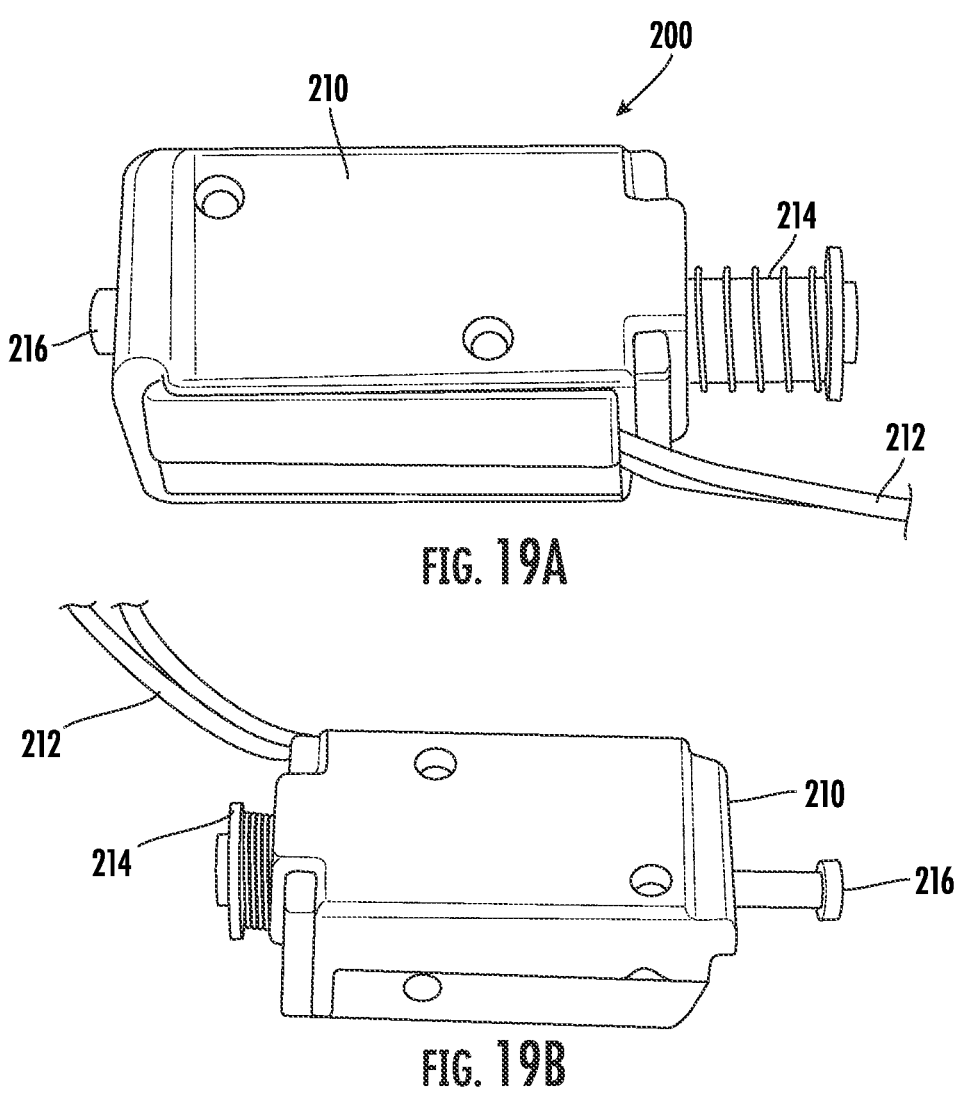
FIG. 19A
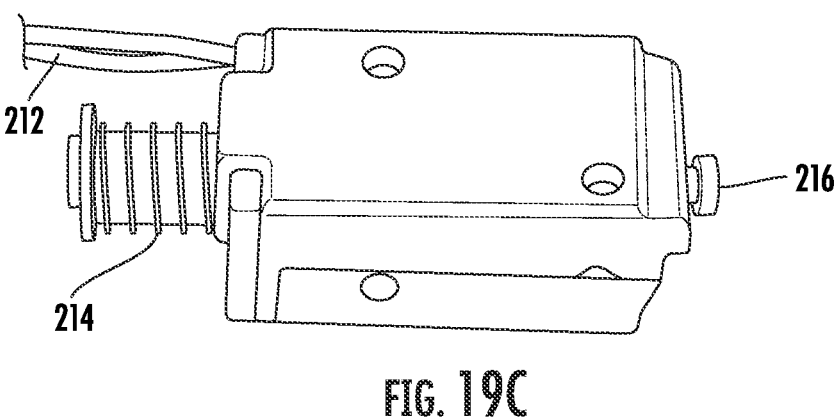
FIG. 19B
FIG. 19C

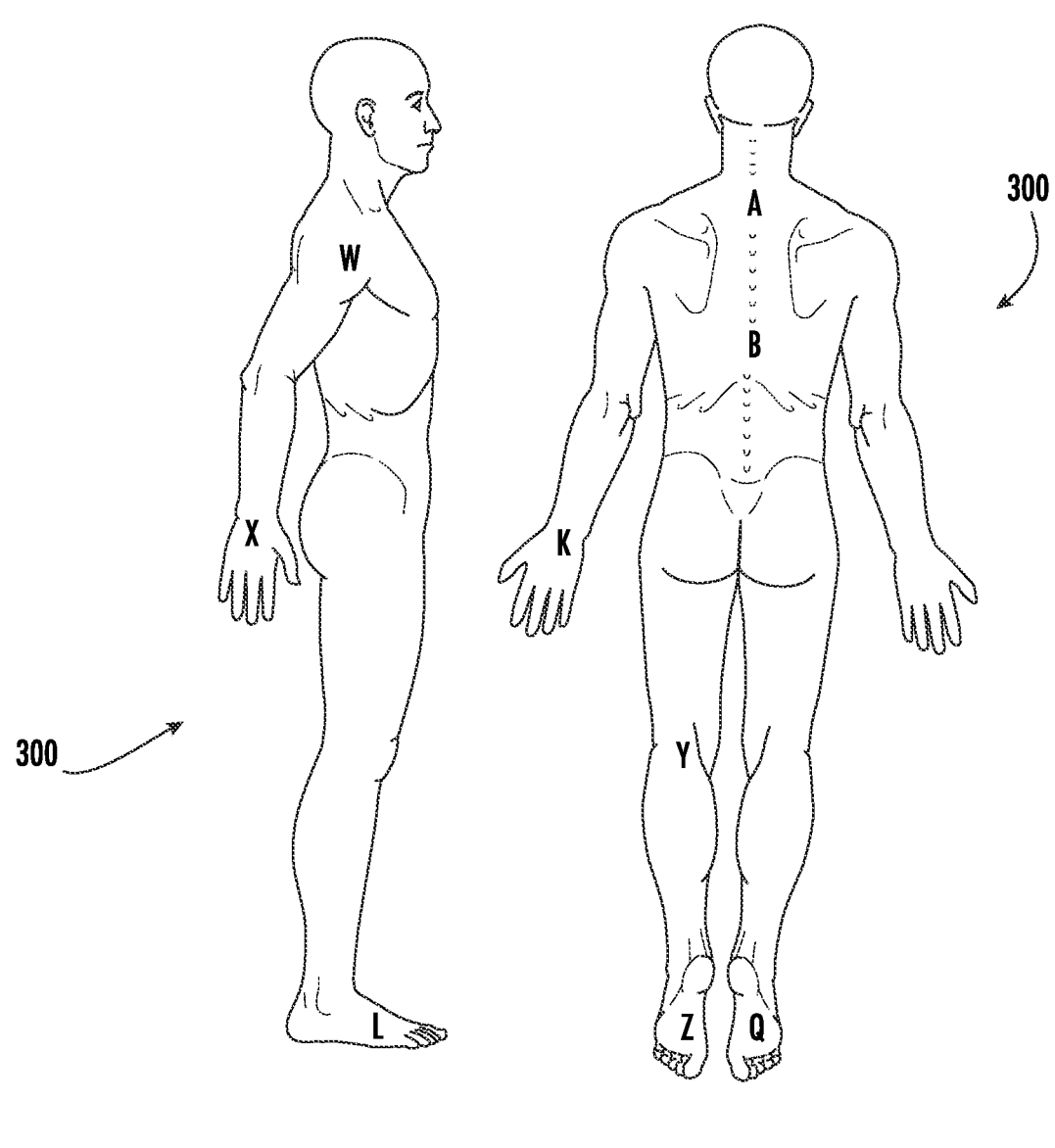
FIG. 20A                    FIG. 20B

ACUPUNCTURE DEVICE AND METHOD OF USING MAGNETIC FIELDS TO STIMULATE ACUPUNCTURE NEEDLES, AND MAGNETIC COIL CONFIGURATIONS

CROSS REFERENCE TO RELATED APPLICATIONS

In accordance with 37 C.F.R. 1.76, a claim of priority is included in an Application Data Sheet filed concurrently herewith. Accordingly, the present invention is a Continuation-In-Part of U.S. patent application Ser. No. 16/585,080, entitled "ACUPUNCTURE DEVICE AND METHOD USING MAGNETIC FIELDS TO STIMULATE ACUPUNCTURE NEEDLES", filed Sep. 27, 2019, which claims priority to U.S. Provisional Patent Application No. 62/738,111, entitled "ACUPUNCTURE DEVICE AND METHOD USING MAGNETIC FIELDS TO STIMULATE ACUPUNCTURE NEEDLES", filed Sep. 28, 2018. The contents of the above referenced applications are incorporated herein by reference in its entirety.

FIELD OF THE INVENTION

The present invention relates to devices and methods used for treating individuals suffering from one or more ailments; to devices and methods for use in acupuncture; to devices and methods using magnetic fields to stimulate needles associated with acupuncture treatments; to devices and methods of generating special magnetic fields; and more particularly, to devices and methods for generating and applying stimulated acupuncture needles to one or more acupuncture points on a body of an individual suffering from one or more ailments using magnetic fields.

BACKGROUND OF THE INVENTION

Acupuncture is a medicinal art finding its roots in Chinese medicine dating back at least 2,500 years. Generally, acupuncture is based on the principle there exists patterns of energy flow throughout the body, and that these energy flows are important to maintaining health and normal body functioning. Disruptions of these flows due to injury, disease or age-related degeneration often results in increased discomfort, contributes to a more rapid degeneration, and in many cases even disease. Stimulation of acupuncture points, i.e. specific points in the body, is believed to help restore or maintain the energy flow, thereby resulting in a healthy body.

Each of the specific acupuncture points in the body are typically stimulated by piercing of the skin and insertion of fine wires or needles, generally referred to as acupuncture needles. It is not uncommon for the acupuncture needles to be rotated or oscillated, typically by the human manipulation of rubbing the inserted acupuncture needle between the acupuncturist's thumb and finger. While such rotation or oscillation is highly beneficial, the technique of human manipulation is always limited by human factors. For instance, the number of needles rotated or oscillated by an acupuncturist is limited to a maximum of two needles at any one time. This can be limiting in the case where an individual seeking treatment requires the insertion of more than two needles. In fact, stimulation of multiple acupuncture points is more of the normal treatment modality. Second, how long the acupuncturist can manually manipulate the acupuncture needles depends on the individual doing the manipulation. Such capabilities can vary from person to person, and even within an individual acupuncturist performing such treatments at different times due to fatigue or other limiting factors. Finally, the speed and/or consistency of manual rotation or oscillation will vary from person to person, and will even vary within a single acupuncturist at various times.

A Transcutaneous Electrical Nerve Stimulation unit, more widely known as a TENS device, is known in the art. TENS is the direct application of micro-current voltages delivered through a set of two conductive adhesive pads applied directly to the skin. TENS systems are used to stimulate various muscle groups through simple galvanic stimulation. TENS systems cause the stimulated muscle(s) to contract, then relax in accordance with user selectable timing cycles of either alternating current stimulation or intermittent direct current. Each can be used for this type of directly applied galvanic muscle stimulation. Applying voltage/current makes the muscle(s) not only contract, but also remain at that level of contraction until the voltage/current stimulating them is no longer applied. TENS systems can be used in acupuncture treatments, with modifications. Such modifications include the use of clips and wires, instead of conductive pads, which directly connect the output of these TENS type devices to the already placed needles at standard acupuncture points. However, these devices were never designed nor intended for this purpose and deliver poorly controlled output levels which vary widely. If not set properly by the clinician before every session, injury may result.

Use of pre-magnetized acupuncture needles is also known in the art. Due to the high cost associated, many such procedures are performed simply by rubbing standard needles against or across magnets to magnetize the needles. Such procedures are problematic, as there are no means to accurately gauge the magnetic properties imparted upon the needles, or even the polarity already set for each pre-magnetized treatment needle to be used. Typically, acupuncture treatments require work on pairs of sites, often employing treatment at multiple sites simultaneously. Unfortunately for the patients, because treatment needles are usually magnetized on site and only moments prior to treatment, each needle is subjected to a wide variety of unequal magnetic qualities and worse. Moreover, because in-house application methods are weak and vary dramatically, they seldom retain the same or even the proper magnetic fields long enough, or at times even the correct polarities needed for effective treatment at paired sites.

Therefore, what is needed in the art is an acupuncture system and method that overcomes the shortcomings of current acupuncture treatments, methods and systems.

SUMMARY OF THE INVENTION

The present invention relates to devices, systems, and methods for generating and applying stimulated acupuncture needles to one or more acupuncture points on a body of an individual suffering from one or more ailments using magnetic fields. The devices and methods are designed to simultaneously stimulate many acupuncture nodes found throughout the body. The devices and methods are designed to deliver either constant or variable magnetic fields that stimulate or 'jiggle' the acupuncture needles. The devices, systems, and methods may use an electromagnetic generator having a standard coil configuration, i.e. a single continuous strand of wire, such as a standard insulated magnetic coil wire. Alternatively, or in combination, the devices and methods may use an electromagnetic generator, which uses a conical wrap configuration or parallel wound configuration, where each 'winding' or complete wrap of wire is treated as an individual layer with its ends joined to the other layers in a fashion that connects each layer or winding in parallel, or wiring configuration wherein each individual wrap of wire is connected/wired in parallel. The parallel wrapped wiring configurations, i.e. connecting each wrap of wire or complete winding layer in parallel with the others, results in dramatically less electrical resistance, which is in accordance with Ohm's law, resulting in a boost of the coil's efficiency that also reduces the required current to generate comparable magnetic fields.

The present devices, systems, and methods have the advantage over known devices and methods of employing a specially designed electromagnetic coil which delivers a programmed, infinitely variable magnetic field while simultaneously bringing additional treatment functions to the acupuncture point locations. The devices and methods can be designed to use magnetic field generators (coils) to induce low level micro-voltage/current within and between pairs of meridian treatment needles. Adjustable intensity can be controlled by varying the applied magnetic field strength that delivers both effects directly to the treatment site. Although it can be employed at a single location, acupuncture treatments are almost always paired with a secondary location for needle insertion. The current devices, systems, and methods employ those same precisely placed acupuncture needles, but further place a specially designed magnetic coil around each pair of meridian needles. Each of the needles can be surrounded by a unique magnetic coil, with the second coil wired/powered in direct opposition. This pair of coils then delivers a precisely opposed polarity effect, one far more effective at stimulating any meridian under treatment. The availability of infinitely variable frequencies allows tremendous flexibility, in addition to ease of tailoring individual treatments to a patient.

As such, the devices, systems, and methods described herein are designed to provide dynamically changing frequency which delivers variable opposed fields, and is flexible enough to accept changes that can be made even while a treatment is in progress. When paired along the acupuncture meridian or extra-ordinary vessel (EV) lines, these alternating micro-current and magnetic fields influence the flow and relative balance along that treatment line (meridian). The opposition of polarity along the meridian or EV line serves to improve acupuncture treatment outcome and has already been noted to result in shorter, more effective treatments.

The devices, systems, and methods are further designed with the ability to simultaneously apply specific wavelengths of visible and invisible light, as well as several other options. Accordingly, the devices, systems, and methods may combine several types of LED's along with a tiny piezo speaker. A wide range of optional light, heat and acoustic therapy can also be applied and even synchronized, adding an additional layer of treatment to those same treatment points, all at selectable intensities, depending upon the specific conditions under treatment.

The devices, systems, and methods may provide for treatment routines which can be available as programs for meridians and specific issues, and to what degree various meridians influence the related organs. A preselected range of frequencies and intensities may be included as part of a standard set of selectable routines, along with an opportunity for the clinician to tailor and store their own preferred routines for various applications and/or clients. To compensate for accommodation effects, the natural tendency that increases tolerance/resistance to any treatment while in progress, small increases in field strength can be selected to increase application levels minutely and incrementally, thereby maintaining treatment levels while increasing effectiveness.

The devices, systems, and methods may utilize various coil shapes and configurations to generate the electromagnetic field. The various coil shapes (conical) along with the style of winding, such as parallel, should contribute to the net efficiency by applying and focusing the magnetic fields directly at the treatment sites. The dramatically reduced electrical resistance of these designs reduces treatment power requirements, while also reducing what might otherwise be substantial resistance heat generated by standard coils. These advances allow for safer treatments of longer duration when required, and deliver far more effective treatments requiring substantially less power while improving treatment efficacy.

As an enhancement to the standard wired connections usually required, the devices, systems, and methods may utilize wireless communication methods, such as Bluetooth. A Bluetooth enabled modular treatment pair will eliminate direct wired connections between the driver and delivery elements located at treatment sites. These can be held in place with simple limb mounting cuffs and/or disposable skin contact collar sticky pads, with specific treatments either directly controlled or with the ability to have a treatment regimen downloaded wirelessly to each module from its controller. This would then free the controller itself to be used with another client.

Accordingly, it is an objective of the invention to provide a device or system for using magnetic fields to stimulate acupuncture needles.

It is a further objective of the invention to provide a method using magnetic fields to stimulate acupuncture needles.

It is yet another objective of the invention to provide a device or system capable of delivering constant magnetic fields to stimulate acupuncture needles.

It is a still further objective of the invention to provide a device or system capable of delivering variable magnetic fields to stimulate acupuncture needles.

It is a further objective of the invention to provide a device or system capable of delivering micro currents which are generated between acupuncture needle sets, and which also stimulate the nodes being treated.

It is yet another objective of the invention to provide a device or system capable of delivering or providing a magnetic field sufficient to stimulate an acupuncture needle, thereby delivering a stimulating effect to the nodes being treated.

It is a still further objective of the invention to provide a device or system capable of automated, simultaneous stimulation of multiple node sets.

It is a further objective of the invention to provide a device or system which can be used by a clinician or patient to provide acupuncture treatment to one or more nodes in a set and go manner.

It is yet another objective of the invention to provide a device or system for using magnetic fields to stimulate acupuncture needles which is capable of providing one or more energy wavelengths, such as ultraviolet light.

It is yet another objective of the invention to provide a device or system for using magnetic fields to stimulate acupuncture needles which is capable of providing one or more energy wavelengths, such as infrared light.

It is a still further objective of the invention to provide a device or system for using magnetic fields to stimulate acupuncture needles which is capable of providing one or more energy wavelengths, such as one or more visible colored light.

It is a further objective of the invention to provide a device or system for using magnetic fields to stimulate acupuncture needles which is capable of providing one or more energy wavelengths, such as one or more sonic frequencies.

It is yet another objective of the invention to provide a device or system for using magnetic fields to stimulate acupuncture needles which uses an electromagnetic coil.

It is a further objective of the invention to provide a device or system for using magnetic fields to stimulate acupuncture needles which uses a standard electromagnetic coil.

It is yet another objective of the invention to provide a device or system for using magnetic fields to stimulate acupuncture needles which uses an electromagnetic conical coil.

It is yet another objective of the invention to provide a device or system for using magnetic fields to stimulate acupuncture needles which uses an electromagnetic conical coil using either standard or various types of parallel wiring.

It is yet another objective of the invention to provide a method of acupuncture treatment using or delivering constant magnetic fields to stimulate acupuncture needles.

It is a still further objective of the invention to provide a method of acupuncture treatment using or delivering variable magnetic fields to stimulate acupuncture needles.

It is a further objective of the invention to provide a method of acupuncture treatment using or delivering micro currents which are generated between acupuncture points, and which also stimulates the nodes being treated.

It is yet another objective of the invention to provide a method of acupuncture treatment using or delivering a magnetic field sufficient to stimulate an acupuncture needle, thereby delivering a stimulating effect to the nodes being treated.

It is a still further objective of the invention to provide a method of acupuncture treatment using or delivering automated, simultaneous stimulation of multiple node sets.

It is yet another objective of the invention to provide a method of acupuncture treatment using or delivering constant magnetic fields to stimulate acupuncture needles, in combination with one or more energy wavelengths, such as ultraviolet light.

It is a still further objective of the invention to provide a method of acupuncture treatment using or delivering constant magnetic fields to stimulate acupuncture needles, in combination with one or more energy wavelengths, such as infrared light.

It is a still further objective of the invention to provide a method of acupuncture treatment using or delivering constant magnetic fields to stimulate acupuncture needles, in combination with one or more energy wavelengths, such as one or more visible colored light.

It is yet another objective of the invention to provide a method of acupuncture treatment using or delivering constant magnetic fields to stimulate acupuncture needles, in combination with one or more energy wavelengths, such as one or more sonic frequencies.

It is a still further objective of the invention to provide various magnetic coil configurations.

It is yet another objective of the invention to provide magnetic coil configurations which are wired in parallel.

It is a still further objective of the invention to provide magnetic coil configurations having a coil or wire with individual windings wound around a cylindrical coil core/form in an uneven manner.

It is yet another objective of the invention to provide magnetic coil configurations having a coil or wire with individual windings wound around a cylindrical coil core/form with more windings at one end.

It is a still further objective of the invention to provide magnetic coil configurations where the magnetic coils or wires are arranged having a connection gap being parallel to a longitudinal axis of a form.

It is a still further objective of the invention to provide magnetic coil configurations where the magnetic coils or wires are arranged having a connection gap perpendicular to the longitudinal axis of a form.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 1 is a schematic diagram of an illustrative embodiment of an acupuncture device configured for generating magnetic fields to stimulate acupuncture without using manual, human manipulation;

FIG. 2 illustrates a top view of the magnetic field generating unit, with the one or more additional treatment members;

FIG. 3 illustrates a bottom view of the magnetic field generating unit, with the one or more additional treatment members;

FIG. 4 illustrates an embodiment of the magnetic field generating unit, without one or more additional treatment members;

FIG. 5A is a perspective view of an illustrative example of a magnetic field generating unit;

FIG. 5B is a top perspective view of an alternative example of the magnetic field generating unit;

FIG. 5C is a bottom perspective view of the magnetic field generating unit shown in FIG. 5B;

FIG. 6A is a perspective view of an illustrative example of the magnetic field generating unit shown in FIG. 5A, with an acupuncture needle inserted therein;

FIG. 6B is a perspective view of an illustrative example of the magnetic field generating unit shown in FIG. 5B, with an acupuncture needle inserted therein;

FIG. 7 illustrates a typical standard circular wound coil with a single electromagnetic coil wound around the main body, and illustrates the magnetic fields generated when electricity is applied to the coils;

FIG. 8 illustrates an embodiment of the acupuncture device with multiple acupuncture needle stimulation units;

FIG. 19A is an illustrative embodiment of a mechanical thumping stimulation unit;

FIG. 19B illustrates the mechanical thumping stimulation unit prior to delivering a thump to an acupuncture or acupressure point;

FIG. 19C illustrates the mechanical thumping stimulation unit post-delivery of a thump to an acupuncture or acupressure point;

FIG. 20A illustrates the general concept of pair placement shown on the human body;

FIG. 20B illustrates the general concept of pair placement shown on the human body.

DETAILED DESCRIPTION OF THE INVENTION

Figure 9:
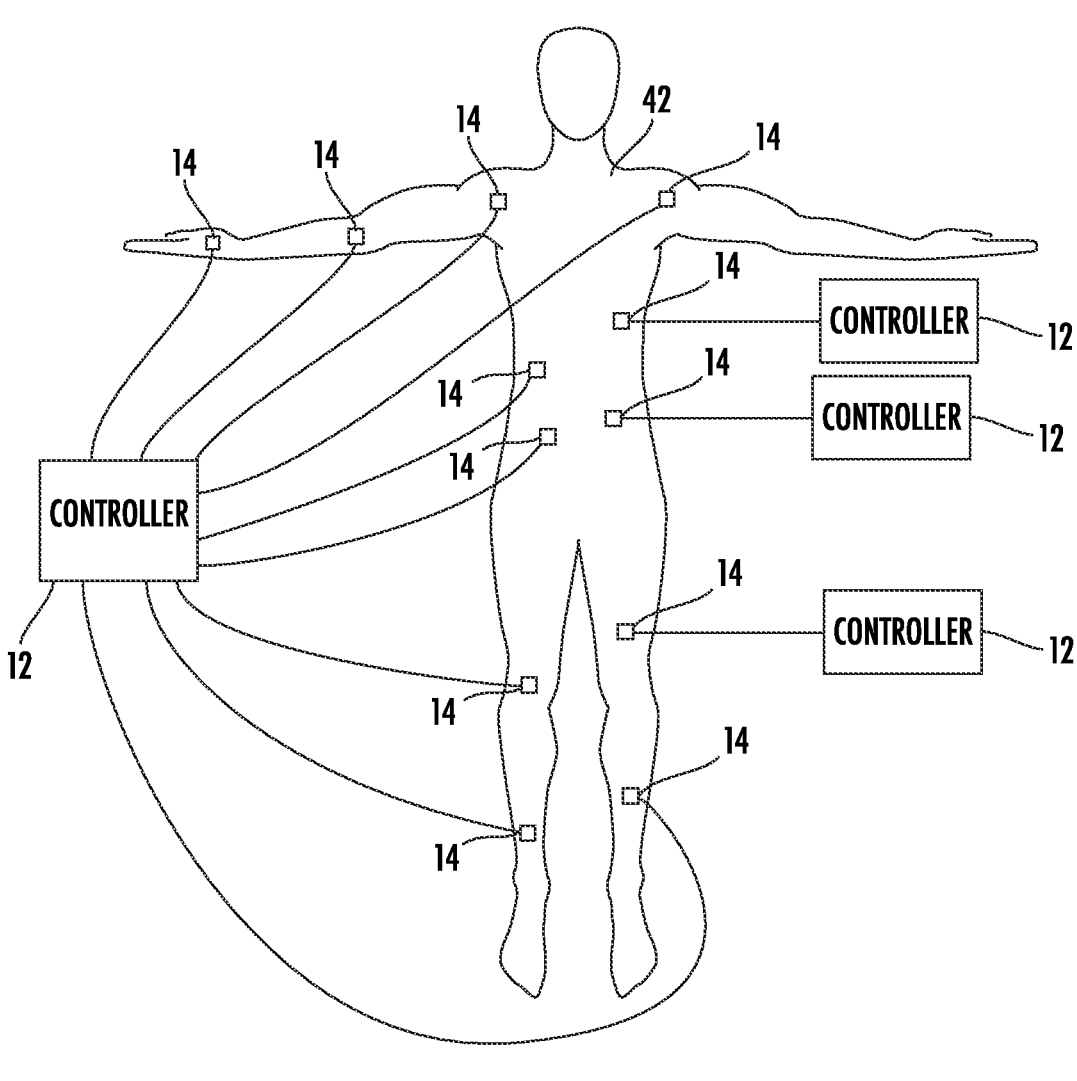
FIG. 9 illustrates the acupuncture device applied to a body for treatment of one or more nodes.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

The present invention provides acupuncture treatment systems and methods which allow the simultaneous treatment, such as, but not limited to, 1-4 pairs of treatment nodes (8 corresponding sites), with fully synchronized 'jiggling needles', light, heat, audio, or combinations thereof. The systems and methods may further provide polarized magnetic fields and low level electrical simulation, and if any, extremely low level electrical stimulation to those nodes. The acupuncture treatment systems and methods may employ an electrically generated pulsating electro-magnetic force field that not only 'jiggles' multiple sets of treatment needles simultaneously with opposing magnetic poles, it adds multiple energies to each site. The opposing poles may include paired units, with the paired units having a north-south-south-north alignment. The acupuncture treatment systems and methods are configured to flip the magnetic polarity in synchronization where the polarity flips back and forth based on a particular frequency used (variable mode). Such acupuncture treatment systems and methods enable acupuncture clinicians to treat one site, a set of sites, or to utilize multiple sites, i.e. 4 site sets (8 treatment sites) simultaneously. The acupuncture treatment systems and methods may utilize needles, preferably steel needles, which are easily excited by the unique electro-magnetic field created by the coil design. The electro-magnetic field may generate the tiniest electrical potential within the needle, delivering that potential directly to the node under treatment. When synchronized (flipping polarity at the same time), opposed cyclic fields are applied to corresponding nodes, it maximizes the treatment's effectiveness. The acupuncture treatment systems and methods may utilize opposite magnetic and electrical potentials created at every set of sites under treatment using frequencies selected by the clinician for specific treatments, resulting in more effective treatment with positive results that last longer. The acupuncture treatment systems and methods may also be configured where the paired units do not flip or change polarity (constant mode). As such, the acupuncture treatment systems and methods can be configured to use or deliver a variable mode, a constant mode, or combinations thereof.

Referring to FIG. 1, a schematic diagram of an illustrative embodiment of a device configured for generating magnetic fields to stimulate acupuncture without using human manual manipulation, referred to generally as acupuncture device 10, is illustrated. The acupuncture device 10 is shown having a controller or control unit 12 and one or more acupuncture needle stimulation units 14, referred to also as pads. Each one or more acupuncture needle stimulation unit 14 is functionally connected to the control unit 12 by a cable or lead 16. The control unit may include a variable frequency generator configured to deliver various power levels, direct voltages, or a combination of various power levels and direct voltages, to the acupuncture needle stimulation units 14. While the control unit 12 is shown delivering electricity to the acupuncture needle stimulation units 14 directly, i.e. wired via cables or leads, electricity can be delivered indirectly by remotely controlled operations, such as battery powered coils.

The control unit 12 is configured to control or modify one or more operational parameters of the acupuncture device 10. The control unit 12 may simply be a printed circuit board with the necessary integrated circuitry. Alternatively, the control unit 12 might be a computer having the necessary hardware for processing capability, storage capability, and any necessary software to drive or control the functioning of various components; and may include, for example, logic boards such as printed circuit boards with the necessary integrated circuitry, central processing units, RAM, ROM, and/or hard drives.

The acupuncture needle stimulation units 14 comprise a support structure 18, a magnetic generator 19, and one or more additional treatment applicators 20A, 20B, 20C, or 20D. FIG. 2 illustrates a top view of the acupuncture needle stimulation unit 14, with the one or more additional treatment applicators 20A, 20B, 20C, or 20D shown in broken lines to indicate their position on a surface opposite of the top surface 22. FIG. 3 illustrates a bottom view of the acupuncture needle stimulation unit 14, with the one or more additional treatment applicators 20A, 20B, 20C, or 20D positioned within the bottom surface 24.

The one or more additional treatment applicators 20A, 20B, 20C, or 20D are configured to provide a treatment modality option that differs from the generation of a magnetic field. The one or more additional treatment applicators 20A, 20B, 20C, or 20D may provide for the application of additional energy wavelengths to an individual in need of acupuncture treatment, such as, ultraviolet 20A, infrared 20B, various colors (i.e. color temperatures of light) 20C, various sonic frequencies 20D, or any combination thereof. For example, in one illustrative example, the acupuncture needle stimulation unit 14 may include all infrared treatment applicators 20B. In another illustrative example, the acupuncture needle stimulation unit 14 may include all ultraviolet 20A or all sonic frequency applicators 20D. In another illustrative example, acupuncture needle stimulation units 14 may be various colors 20C, such as LEDs delivering only blue wavelengths of colored light. In another illustrative example, the acupuncture needle stimulation units 14 may be a mixture of various colors 20C, such as two (2) blue colored LEDs and two (2) red LEDs. While described as having two LEDs, one or more than two may be used. In another illustrative embodiment, the acupuncture needle stimulation units 14 may include two (2) ultraviolet 20A and two (2) infrared treatment applicators 20B. While the acupuncture needle stimulation unit 14 is described as having four (4) treatment applicators, 20A, 20B, 20C, or 20D, the acupuncture needle stimulation unit 14 may have as many applicators as necessary to provide the desired effect, including but not limited to 6-20, including 6, 8, 10, 12, 14, 16, or 18. FIG. 4 illustrates an embodiment of the acupuncture needle stimulation unit 14 without one or more additional treatment applicators 20A, 20B, 20C, or 20D. The treatment applicators 20A-20D may be configured to provide a synchronous cycle, such as a synchronous cycle of a routine of LED light patterns cycles, such as around the circumference of the pad, colors appear in a clockwise (or counter-clockwise) sequence throughout the visible range of single or multiple colors, such as blue, yellow, orange, red, and green; colors appear in a clockwise (or counter-clockwise) sequence throughout the visible (or if desired, invisible) range, and then pulse in sequence through a range of single or multiple colors, or wavelengths of light, such as blue, yellow, orange, red, and green; or pulse in sequence through a range of single or multiple colors, such as blue, yellow, orange, red, and green.

Referring to FIG. 5A and FIG. 6A, a perspective view of the acupuncture needle stimulation unit 14 utilizing an electromagnetic unit 25 (having a magnetic generator 19) is shown. The electromagnetic unit 25 with magnetic generator 19 is shown having a main body 26 extending upwardly and away from the top surface 22 of the acupuncture needle stimulation unit 14. The main body 26 has a first open end 28 and a second opposing end 30. The second end 30 is integrally formed from, or attached and secured to, the acupuncture needle stimulation unit 14. The first open end 28 exposes an internal lumen 32 which is sized and shaped to receive and hold an acupuncture needle 34 (preferably by sliding over an acupuncture needle 34 that has been inserted into the patient). An electromagnetic coil 36 is wrapped around the main body 26. When needed, an acupuncture practitioner can simply move or slide the acupuncture needle 34 into the inner lumen 32, see arrows 35, FIG. 5A. Once inserted, the acupuncture needle 34 rests within, see FIG. 6A. Preferably, the acupuncture needle 34 is made from a ferrous material.

Referring to FIG. 5B, FIG. 5C, and FIG. 6A, a perspective view of an alternative embodiment of the acupuncture needle stimulation unit 14 utilizing an electromagnetic unit 25 with a magnetic generator 19 is shown. The acupuncture needle stimulation unit 14 shown in these figures has a generally circular shaped main body 26. The electromagnetic unit 25 with magnetic generator 19 is shown housed within a main body 26, instead of extending upwardly and away from the top surface 22. The main body 26 has a first open end 28 and a second opposing end 30. The first open end 28 exposes an internal lumen 32 which houses or forms the electromagnetic unit 25 with magnetic generator 19. The internal lumen 32 or the electromagnetic unit 25 with magnetic generator 19 is sized and shaped to receive and hold an acupuncture needle 34 (preferably by sliding over an acupuncture needle 34 that has been inserted into the patient). The electromagnetic unit 25 preferably includes an electromagnetic coil 36. When needed, an acupuncture practitioner can simply move or slide the acupuncture needle 34 into the inner lumen 32, see arrow 35, FIG. 5B. Once inserted, the acupuncture needle 34 rests within, see FIG. 6B. FIG. 5C illustrates the bottom surface 24 with a plurality of LED treatment applicators 20A oriented around the perimeter.

When the acupuncture needle 34 is inserted into the main body 26, the acupuncture needle is in a position to be surrounded by the electromagnetic coil 36. One or more frequencies applied to the electromagnetic coil 36 by the controller 12 results in stimulation, i.e. jiggling of the acupuncture needle 34. Once the frequencies are applied and energize the electromagnetic coil 36, the acupuncture needle 34 is constantly "jiggled" at a resonant rate, which is dependent upon the frequency applied. FIG. 7 illustrates a typical standard circular wound coil in which a single electromagnetic coil 36 is wound around the main body 26, thus generating the magnetic fields illustrated by the standard magnetic lines of force 38 and 40.

Various types of magnetic generators 19 might be used to provide an electromagnetic field.

As used herein, "a wrap of wire" is defined as comprising of a (one) single continuous turn of wire around any core. As used herein, "a winding of wire" is defined or consists of a (one) single wire wrapped continuously around a core of any shape and covers that core in a single layer of wire from one end to the other end. These windings are terminated at each end, and those terminations are connected so that each winding is wired in parallel.

One magnetic generator 19 may include any type of coil, regardless of how it may be wired, wound around a conical form or core shaped roughly like a funnel. This embodiment produces a unique and unusually shaped magnetic field, in which the magnetic field generated is wider at one end and narrower at the opposite end.

One magnetic generator 19 may include any type of coil form where the individual windings (a single winding completely covering any shape core with one layer from end to end), that are electrically connected at their natural terminations, located at opposite ends of the coil form. Each (all) continuous complete windings or layers of wire that terminate at each end of the form are electrically bonded together at the beginning and end of each individual winding or complete layer around any type core, thereby connecting each and every full winding of wire around the core in parallel. In accordance with Ohm's law, this unique way of wiring the coil greatly reduces its natural electrical resistance, allowing it to consume less power while still capable of delivering the same results. Wiring of this kind will reduce cost yet still be able to deliver the same magnetic fields.

One magnetic generator 19 may include any variety of parallel wired coil, such as any type of coil form wherein the individual wraps are electrically connected in parallel at their terminations after wrapping only once around the coil form (as defined herein, a wrap goes around the coil form but always covers less than 360 degrees). This method is suitable for standard as well as conically wound coils. Each (all) continuous full wraps of wire are electrically bonded at the beginning and end of each individual wrap or turn of wire around the core, thereby connecting each and every full wrap (of less than 360 degrees) around the coil core in parallel. In accordance with Ohm's law, this unique way of wiring the coil greatly reduces its natural electrical resistance, allowing it to consume less power while still capable of delivering the same or improved results. Wiring of this kind will reduce cost yet still be able to deliver the same magnetic fields.

One magnetic generator 19 may include any type of coil form, although probably best suited where a cylindrical core/form is desired/required as well as a conical magnetic field). Such magnetic generator 19 is a design in which the individual windings (usually a single continuous winding of wire) are wound around a cylindrical coil core/form in an uneven fashion, with the majority of its windings located at one end of the core/form. This delivers a visual form similar to the conical coil described above, yet there remains an important difference because the majority of windings are located at only one end of the form; that end will produce a wider and more powerful magnetic field when energized. Conversely, the opposite end will produce a narrower, less powerful, yet more focused magnetic field. This type of coil (conically wound on a cylindrical core) has a greater percentage of its windings concentrated at one (either) end of the core/form.

In use, an acupuncture practitioner would place one or more acupuncture needle stimulation units 14 to one or more nodes of a patient that requires an acupuncture treatment. Because it is necessary to physically locate the acupuncture points first, they vary slightly with each individual. As a result, it is preferable to locate a node, place the acupuncture needle 34 therein, and slip or move the stimulation unit 14 in place over the acupuncture needle 34. Once each of the one or more acupuncture needle stimulation units 14 are in place, when electricity is applied, the electromagnetic coil 36 causes the acupuncture needle 34 to jiggle in resonance with the selected and applied frequency. Application of different frequencies results in different levels of stimulation/treatment. Unlike permanent magnet therapy or premagnetized needles, which are dependent upon weak static charges retained by, but limited by the composition and actual magnetization of the needles themselves, the acupuncture device 10 and delivery method employs an induced magnetic field within the treatment needle (acupuncture needle 34) itself. As such, the acupuncture device 10 and methods allow for precisely controlled levels of treatment which can be constant or variable. Additionally, the current treatment itself can be varied at any time during treatment or at preselected intervals during the application, allowing for an almost infinitely variable regimen which is easily tailored to the individual being treated. Specific treatment regimens may be selected from a selection of treatments or stored in the device memory for ongoing or practitioner favored treatments. In addition to the acupuncture needle 34 stimulation, the practitioner may also choose to deliver other sources of energy to the patient simultaneously, i.e. ultraviolet light treatment, infrared light treatment, visible colored light treatment, sonic frequencies treatment, or combinations thereof, before, during or after an acupuncture treatment, by using the treatment applicators 20A, 20B, 20C, or 20D to deliver the appropriate energy to the appropriate node.

While the acupuncture device 10 is shown having one acupuncture needle stimulation unit 14, most acupuncture treatments require stimulation of multiple nodes. As such, the acupuncture device 10 is preferably configured with multiple acupuncture needle stimulation units 14, see FIG. 8. In FIG. 8, the acupuncture device 10 is shown with multiple acupuncture needle stimulation units 14 connected to a single controller 12, see also FIG. 9. Alternatively, individual controllers 12 can be secured to a single acupuncture needle stimulation unit 14 applied to different nodes along the body 42, see FIG. 9. The multiple acupuncture needle stimulation units 14 can be used with the sane frequencies or at different frequencies and can jiggle the needle 34 at the same time or at different times.

The method and device in accordance with the present invention provides for constantly agitated acupuncture needles without using manual labor, i.e. the practitioner agitating the acupuncture needles by hand. Under such treatment, the patient is provided with a method of providing the stimulation, i.e. jiggling or agitating of more than two acupuncture needles at one time and across larger portions of the body. The acupuncture device 10 provides for various acupuncture treatments, which include 1) acupuncture needles in constant motion, i.e. continuous, alternating stimulation and therefore jiggling, 2) acupuncture needles constantly varying magnetic polarity generated by fluctuating, alternating current, 3) acupuncture needles delivering constantly varying micro voltages induced by magnetic coils, 4) acupuncture combined with Photonic Stimulation (various color temperatures—wavelengths of light) around the acupuncture needle coils, or 5) acupuncture combined with deep audio stimulation at the acupuncture needle coils. The acupuncture needles 34 may also be magnetically stimulated by alternating or non-alternating current (direct current), which would induce constant magnetic properties as well as a constant micro voltage to the node(s) being treated.

Figures 10A, 10B, 11:
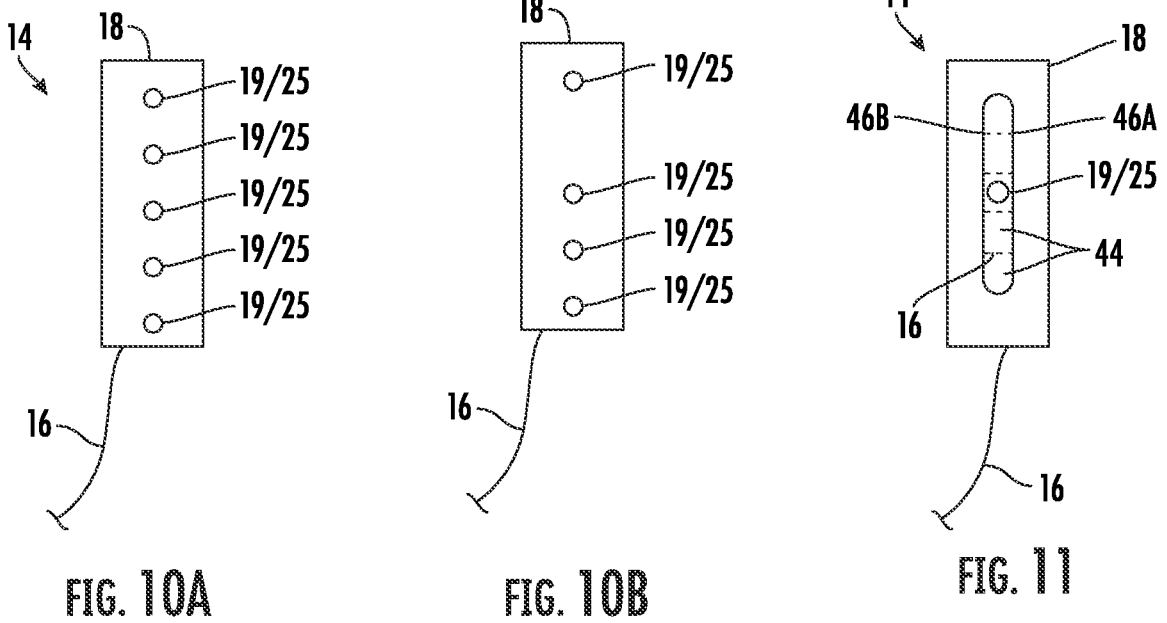
FIG. 10A illustrates the acupuncture device having multiple acupuncture needle stimulation units.
FIG. 10B illustrates the acupuncture device having multiple acupuncture needle stimulation units arranged in a non-uniform pattern.
FIG. 11 illustrates an acupuncture needle stimulation unit having a support structure with a movable magnetic generator.

FIGS. 10A-11 illustrate alternative embodiments of the acupuncture needle stimulation unit 14. FIG. 10A provides an acupuncture needle stimulation unit 14 having a support structure 18 with multiple magnetic generators 19 (or electromagnetic units 25). In this configuration, a practitioner can place the support structure 18 to the body and be able to apply treatment to multiple nodes through the multiple magnetic generators 19 or electromagnetic units 25. While FIG. 10A illustrates the multiple magnetic generators 19 or electromagnetic units 25 being evenly spaced apart about the support structure 18, the multiple magnetic generators 19 or electromagnetic units 25 need not be evenly spaced apart or arranged in a uniform pattern, see FIG. 10B.

FIG. 11 illustrates an acupuncture needle stimulation unit 14 having a support structure 18 with a movable magnetic generator 19 (or electromagnetic unit 25). Such embodiment allows the practitioner the capability to place the acupuncture needle stimulation unit 14 on a portion of a body, and move the acupuncture needle stimulation unit 14 to a particular location. A slotted opening 44 allows the magnetic generator 19 to slidably move to a position within the slotted area. A plurality of stops, right stop 46A and left stop 46B, maintain the movable magnetic generator 19 in a predetermined position. Accordingly, the right stop 46A and left stop 46B may be made of a plastic material that gives when a sufficient force is applied thereto, but remains firm when the force is not applied. The magnetic generator 19 may be secured to channels (not shown) located on the bottom surface of the support structure 18 that allow it to move directionally, forwards or backwards, within the slotted opening 44.

Figures 12, 13:
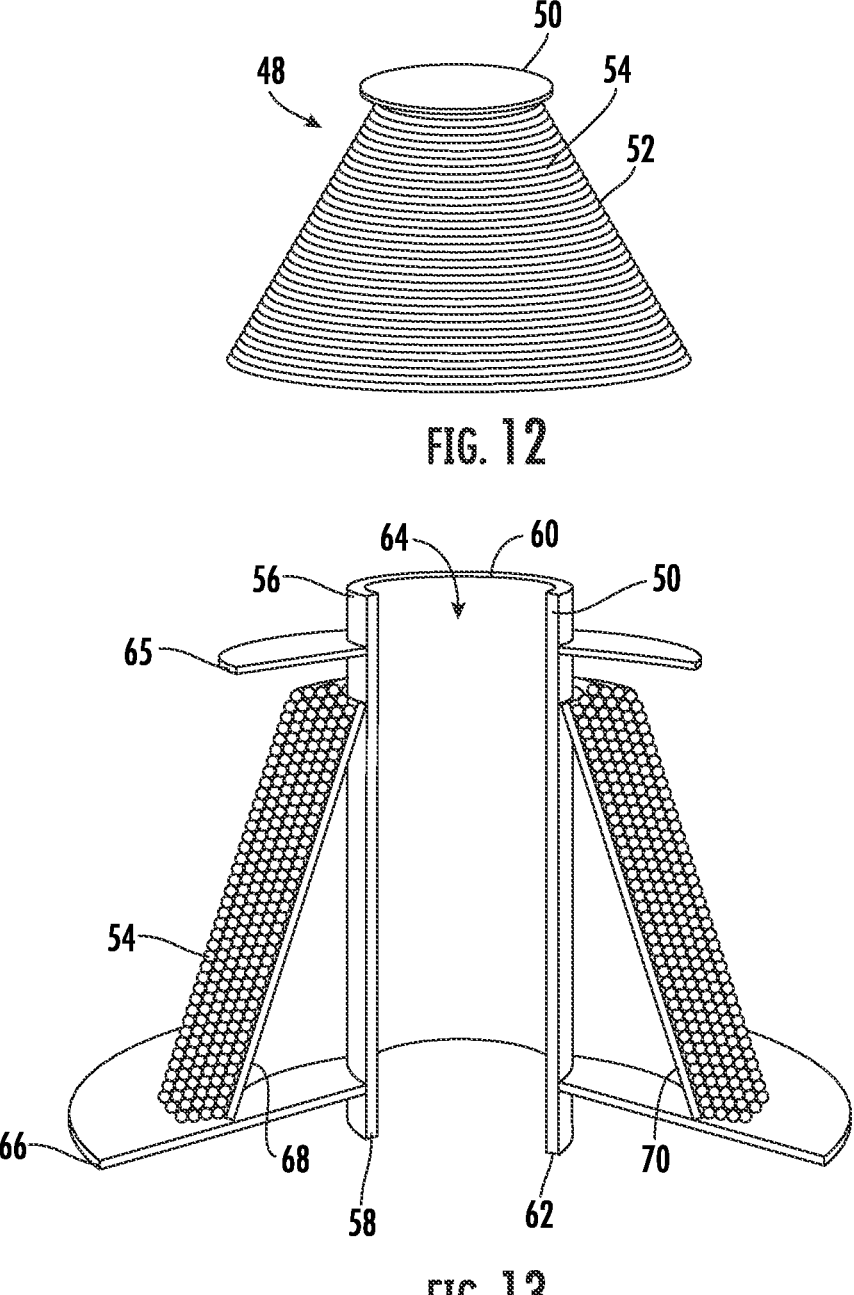
FIG. 12 illustrates an embodiment of an electromagnetic conical magnetic field generator.
FIG. 13 is a cross sectional view of the electromagnetic conical magnetic field generator embodiment.

FIG. 12 illustrates an embodiment of the magnetic field generator 19, illustrated as an electromagnetic conical magnetic field generator 48. The electromagnetic conical magnetic field generator 48 comprises a cylindrical center 50 with a conical surface 52 having a coil or wire 54 wrapped there around, thus forming a magnetic conical coil. The magnetic coil or wire 54 can consist of a single wire wrapped from one end to the other and back again, over and over, in much the same manner as a fishing reel winds its line in layer after continuous layer.

FIG. 13 is a cross sectional view of the electromagnetic conical magnetic field generator 48. The cylindrical center 50 has a first end 56 and a second opposing end 58. The first end 56 and the second end 58 may have openings 60 and 62, thereby exposing an internal passageway 64, which preferably spans the distance from the first end 56 to the second end 58. The electromagnetic conical magnetic field generator 48 may include a first disc 65 positioned at or near the first end 56, and a second disc 66, positioned at or near the second end 58. A pair of angled side walls 68 and 70, integrally formed from or secured to the cylindrical center 50, extend outwardly away from the cylindrical center 50, terminating at the second disc 66.

Figure 14:
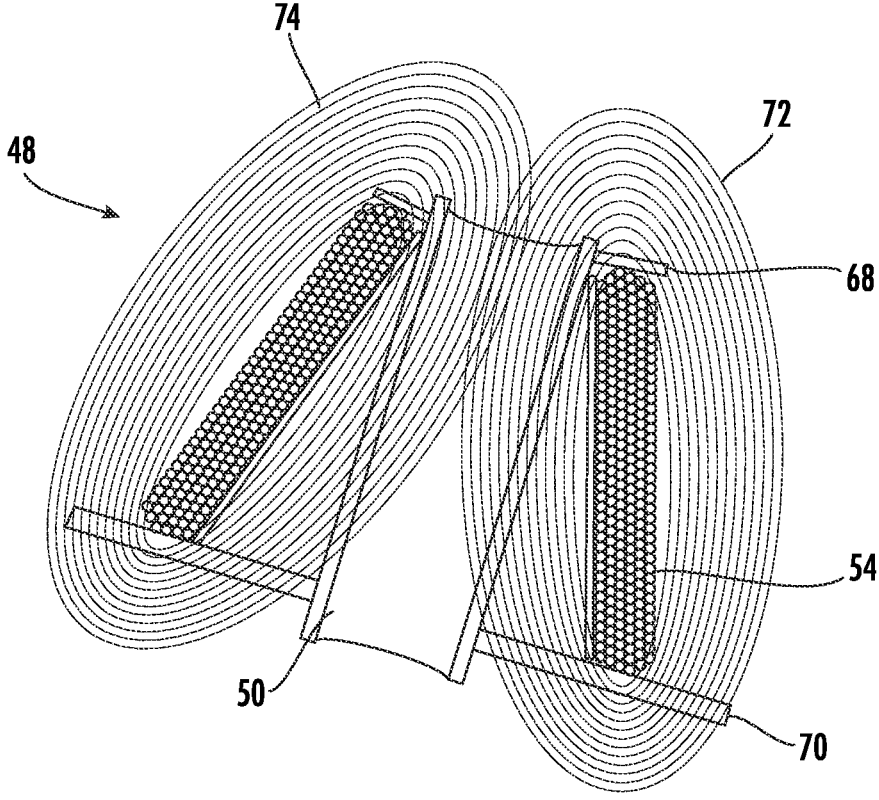
FIG. 14 illustrates the magnetic field lines generated by the electromagnetic conical magnetic field generator.
Figure 15A:
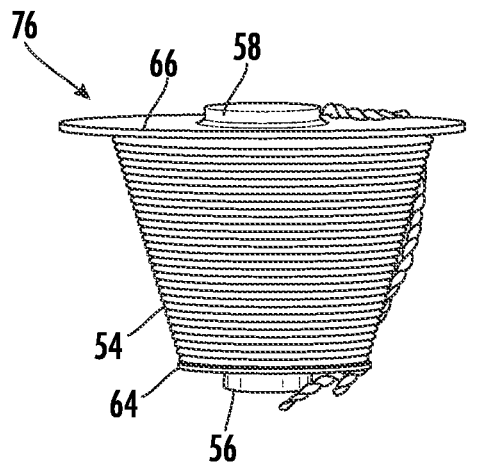
FIG. 15A illustrates an embodiment of a parallel wired coiled conical magnetic field generator.
Figure 15B:
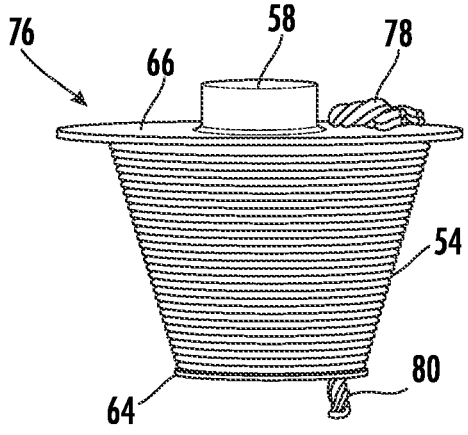
FIG. 15B is an alternative view of the parallel wired coiled conical magnetic field generator.
Figures 16A, 16B:
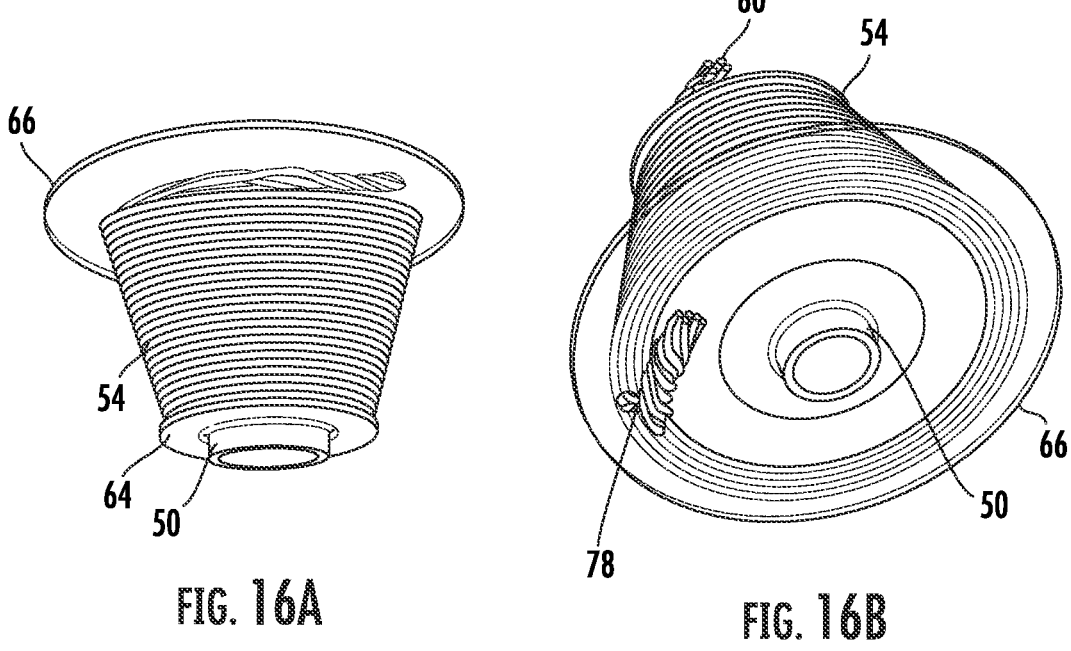
FIG. 16A is an alternative view of the parallel wired coiled conical magnetic field generator.
FIG. 16B is an alternative view of the parallel wired coiled conical magnetic field generator.

The angled side walls 68 and 70 provide the electromagnetic conical magnetic field generator 48 with an overall conical shape. As shown, the magnetic coil or wire 54 is wrapped around the cylindrical center 50. FIG. 14 illustrates the magnetic field lines of force 74 generated by the conically wound coil or wire 54. The magnetic field generated creates a V-shaped field having wide magnetic field lines which taper to a central area or point. With the wide end (second end) 58 of the cone towards the treatment site, a less intense magnetic field would be applied. Conversely, with the narrow end (first end) 56 of the cone towards the treatment site, a more intense magnetic field may be delivered below the skin and directly to the meridian node under treatment.

The electromagnetic conical magnetic field generator 48, as in any magnetic field, is known to move or activate ferrous materials, and in many applications non-ferrous or non-ferrous and mixed materials, employed as plungers in a different manner than standard coils. Energizing a standard solenoid drives its plunger full force and all at once in a single sustained motion. Energizing an electromagnetic conical magnetic field generator 48 is believed to move its plunger slower and less powerfully at the wide end. As the plunger moves toward the narrow or more magnetically concentrated end, speed and force increases as the plunger is propelled forward by the more concentrated magnetic fields. This achieves something never accomplished by any coil, variable speed nonlinear plunger activation/motion/movement, and the extent as well as the force of this movement can be controlled by simply varying the shape and applied voltage. Since the potential conical shape and size of the electromagnetic conical magnetic field generator 48 is virtually limitless, the electromagnetic conical magnetic field generator 48 form itself is adaptable enough to fill the needs of practically any application that could benefit from the use of this type coil to either move a plunger or utilize its uniquely shaped magnetic fields for other purposes.

Alternatively, the electromagnetic conical magnetic field generator 48 may contain the magnetic coil or wire 54 in which complete wraps are wired in parallel. In a further embodiment, the electromagnetic conical magnetic field generator may contain the magnetic coil or wire 54 in which each individual wind of wire is connected in parallel, referred to specifically as parallel wired coiled conical magnetic field generator 76. While parallel wired coiled conical magnetic field generators 76 are shown in FIGS. 15A-16B as assuming a conical shape, although other shapes may be used. As described above, standard coils are formed by employing a single continuous wire wrapped around the core from one end to the other and back again, over and over, until the desired field strength can be achieved. The parallel wired coiled conical magnetic field generator 76 differs in that each complete layer of wire is a unique wrap unto itself, with each of these layers connected to every other layer, 78 and 80, see FIGS. 15A, 15B, 16A, and 16B, only at both ends of each complete wrap of the coil, where they exit the form. As illustrated in FIGS. 15A-16B, each layer of wire can clearly be seen where it exits the form; and in this example, only after the coil is finished has each layer of wire been connected to the other layers at the opposite ends of the coil form, which is where activation power is applied.

Figure 17:
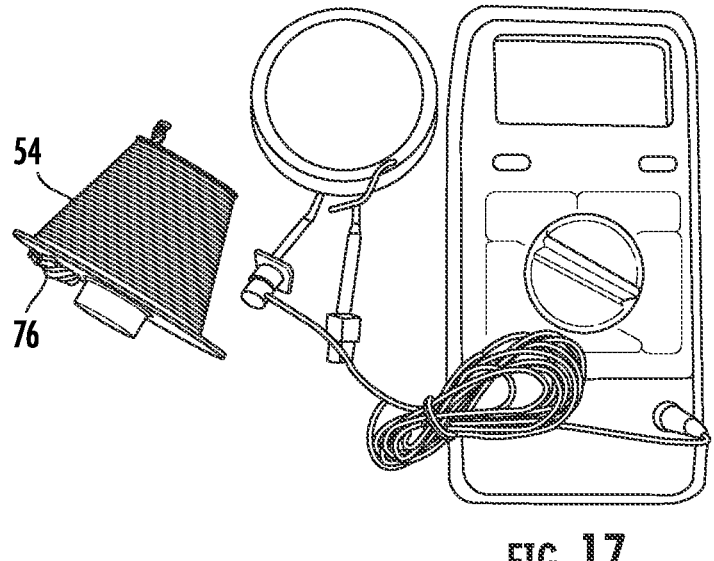
FIG. 17 illustrates a resistance reading associated with a single continuous wire wound around a standard conical spool.
Figure 18:
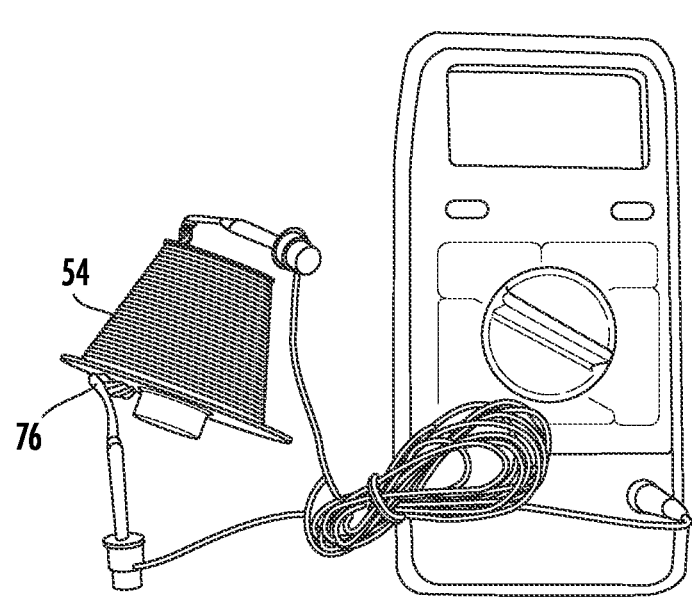
FIG. 18 illustrates a resistance reading associated with a parallel wired coiled conical magnetic field generator.

The parallel wired coiled conical magnetic field generator 76 is believed to reduce electrical resistance dramatically when compared to a standard, continuous wrapped coil. The innovative new way of wiring associated with the parallel wired coiled conical magnetic field generator 76 improves efficiency and reduces energy consumption. Referring to FIG. 17 and FIG. 18, two identical quantities (lengths) of 18-gauge wire 54 from the same source were used. FIG. 17 shows a single continuous wire wound around a standard conical spool as it was delivered. The wire 54 in FIG. 18 comes from an identical spool and is wrapped around a conical form with 10 individual layers, with each separate winding layer wired in parallel. It also comprises individual layers of the same 18-gauge wire 54, which are only connected at the points where they exit the form ends. During testing of the two embodiments, a dramatic difference in resistance was shown, see FIG. 17 and FIG. 18. The embodiment illustrated in FIG. 17 reveals roughly a 75% reduction in electrical resistance at room temperature. Alternatively, parallel wound coils could be configured in a way that connects each individual winding of wire around its core at opposite ends of the coil form.

The acupuncture device 10 may be designed so that it uses one or more different electromagnetic generator types, thus providing unique capabilities to produce a truly broad range of uniquely individual and/or combined magnetic and physical effects. These can be applied to everything from wave guides to metal fabrication. Such acupuncture device 10, and each individual magnetic generator, is capable of improving efficiency and varying the shape of magnetic fields, therefore allowing these new shapes of magnetic fields to be utilized in ways never before conceived.

The acupuncture device 10 and methods, therefore, using any one or combinations of components described herein, provide for a new method of acupuncture having an ultra-precise delivery where the amount of acupuncture needle "jiggle" and/or magnetic field density and/or induced current is delivered directly to either acupuncture or acupressure meridians, or individually selected as a standalone treatment. The fluctuating magnetic fields will also induce movement in the acupuncture needle itself (if used) during treatment. The ability to have variable and individually selectable frequency/power/light/audio settings for as many coil sets as desired for the most beneficial specific treatments can be beneficial to the patient.

The acupuncture device 10 and according methods have provided several benefits. The acupuncture device 10 has provided differences in the efficacy relative to other forms of acupuncture and has shown to consistently deliver a more positive overall impact, and manages to accomplish this in less time. For example, in treatments designed for parasympathetic response (also 'rest and digest' or 'feed and breed'), the patient was shown to drop into this positive state faster with the acupuncture device 10 than with any 'conventional' treatments. Accentuating the parasympathetic response (fuller/slower respiration, slower/fuller pulse attributes, 'happy' gastric sounds reveal a relaxation of the digestive tract and cooling of the extremities (which returns circulation to the torso organs). These levels and others were achieved more quickly via use of the acupuncture device 10, which also allows them to be more accurately controlled. The reduction achieved in levels of adrenalin, noradrenalin, and cortisol are typical of reduced sympathetic response, and these also aid in improving the total therapeutic effect of every treatment.

The application of the acupuncture device 10 enables a reduction in the total treatment time and, in many instances, the total number of needles or treatment points required. This not only allows the clinician access to more patients during the working day, it also delivers a more effective treatment in less time, effectively reducing the practitioners overhead by increasing the number of clients treated per day, while at the same time improving results.

Usage of the acupuncture device 10 treatment pairs on the anterior/sagittal line (Ren-Mai) and posterior/sagittal line (Du-Mai) activates improved responses in the area of glandular and energetic foci, these are most often associated with what Eastern medicine calls chakras. These points/pairs, combined with 'conventional' distal needle placements, impact the entire physiology of each person under treatment. Two, four, or even many more, pairs can be selected by the experienced acupuncturist practitioner to tailor the treatment to the client's ailments, e.g. frontal headache treated with distal pair(s) on the arm(s), or treating the line of large intestine (arm-yangming), which more quickly dissipates and relieves simple discomfort and is also effective in treating more acute pain. The vibration response to an induced magnetic field by individual acupuncture needles (a wide variety of needle configurations are available), is dependent upon the net gauss field strength applied, as well as the specific length, thickness, and mass of each needle. The ferromagnetic content of needles, i.e. iron, cobalt, nickel, manganese, gadolinium, and lodestone, in use also comes into play. However, treatment needles are generally composed of the same or nearly the same combination of basic components, allowing them to be generally considered and treated as virtually identical. Yet, this does not rule out the possibility of needles optimized with specific ferromagnetic content that may prove to be more effective.

The systems and methods using acupuncture device 10 has shown differences in efficiency over other forms of acupuncture. The systems and methods using acupuncture device 10 have shown to consistently deliver a more positive overall impact, and manages to accomplish this in less time. As an illustrative example, in treatments designed for parasympathetic response (also known as "rest and digest" or "feed and breed"), the patients were observed to drop into this positive state faster than with any conventional treatments. Accentuating the parasympathetic response (fuller/slower respiration, slower/fuller pulse attributes, "happy" gastric sounds which reveal a relaxation of the digestive tract and cooling of the extremities (which returns circulation to the torso organs) were achieved more quickly. The reduction achieved in levels of adrenalin, noradrenalin, and cortisol are typical of reduced sympathetic response, and these also aid in improving the total therapeutic effect of every treatment. It is further believed that application of the system and devices in accordance with the present invention enables a reduction in the total treatment time and, in many instances, the total number of needles or treatment points required. This not only allows the clinician access to more patients during the working day, it also delivers a more effective treatment in less time.

Alternative mechanisms for delivering acupuncture stimulation may be used. For example, an acupuncture pressure stimulation unit 200 may be designed to use a mechanical thumping device to deliver an acupuncture treatment. As such, the stimulation unit 200 is designed to use the mechanical thumping, instead of acupuncture needles, to deliver a thump to either acupuncture or acupressure points. The stimulation unit 200 could be designed to stimulate any number of acupuncture points simultaneously, individually, or with any or all of the previously described additional treatment applicators 20A, 20B, 20C, or 20D. This is a treatment. The actual thumper itself would mechanically deliver a pressure or thump to the patient using, for example, but not limited to, an electro mechanical or piezoelectric device. The compact 'thump' delivery devices could easily be held in place with an elastic or loop and hooking style fastening (VELCRO) band, or replaceable self-stick pads; and could even be Bluetooth controlled. The thumper may be designed so that when energy is applied, a thump is delivered (positive thumper). Alternatively, the thumper may be designed so a thump is delivered when de-energized (negative thumper). The positive thumper may be designed to drive a solenoid piston and/or a piezo electric device placed directly against a receiving surface. The negative thumper device could be configured to use the energy of a spring already compressed by energizing the device, delivering the thump when de-energized. Controlling the energy delivered by each thump, mild to maximum, may be achieved by any number of means, such as variable spring pressure or controlling the degree of excitation to the delivery device itself. Bluetooth devices could be configured to be self-contained/rechargeable, powered by a small pack that could be either battery or wall powered and placed on or near the treatment location sufficient to provide the required power. The benefit here is one of eliminating the need for any long connective wiring to each treatment site.

FIGS. 19A-19C illustrate an embodiment of an acupuncture pressure stimulation unit 200 designed to use a mechanical thumping device to deliver an acupuncture treatment. The stimulation unit 200 includes a housing structure 210, a power cord 212, a solenoid 214, and a plunger or piston 216. FIG. 19B illustrates the acupuncture pressure stimulation unit 200 in the "power on pull" position. FIG. 19C illustrates the acupuncture pressure stimulation unit 200 in the "power off push" position.

When the acupuncture pressure stimulation unit 200 is embodied as a solenoid, the thump itself can be delivered by any standard design. To be effective, repetitive and consistent, the thump can be delivered by using preset voltages to energize the solenoid at predetermined levels. An integral spring could be employed to return the plunger or piston 216 to its resting position and ready to be energized for the next thump. An alternate method would be to have the plunger compress a spring that, when de-energized, would allow the spring tension to be released, delivering the thump.

Alternatively, the acupuncture pressure stimulation unit 200 may be embodied as a piezo electric device, i.e. having a crystal that generates electricity when physically activated, and conversely, generates physical activity when electricity is applied.

Clinical Testing

An acupuncture treatment method using the acupuncture device 10 was used over a wide frequency range (1-100,000 Hz) for direct site delivery of magnetic fields with opposing polarity shifts, i.e. between matched acupuncture needle stimulation unit or pad 14 sets, along with such additional stimuli as the clinician may choose and not limited to visible light and/or audio waves originating and delivered directly to each treatment site. The acupuncture device 10 consisted of two major components, a control unit and four matched sets of acupuncture needle stimulation units or pads 14 specifically designed to deliver the subtle effects of opposing magnetic fields and other stimuli. Simultaneous treatment of up to at least eight nodes was possible. 8 Hz was chosen as the primary setting. The acupuncture treatment method utilizes a magnetic field generated within each acupuncture needle stimulation unit or pad 14 (matched pad sets generate opposing fields), and these magnetic fields work to deliver three discrete and very distinct but always repeatable effects at every activation.

First, a discrete opposing magnetic field was delivered by pad sets directly to the nodes under treatment. Second, by varying the magnetic field surrounding a treatment needle, the magnetic field of that needle varied while remaining in perfect sync. Third, this varying magnetic field also induced, within standard treatment needles, a tiny almost imperceptible movement that also remained in perfect sync with the first two effects. Once settings were determined and the acupuncture needle stimulation units or pads 14 placed, the acupuncture device 10 delivered a consistent, repeatable treatment regimen without the need for a clinician in attendance.

Various frequencies, such as, but not limited to 1-100,000 Hz, determined by the acupuncturist were selected and applied for specific treatment regimens, such as various mode (polarity flipping) or constant mode (no polarity flipping or change). The acupuncture treatment method also utilized a synchronous set of LEDs, which were part of the acupuncture needle stimulation unit or pad 14 and ready to deliver a range of visible light to the node under treatment. Discrete visible light wavelengths were included to offer an additional layer of therapeutic stimulation directly to the acupuncture sites. Sound was also available at the treatment site if the clinician wishes to deliver audio as well (.mp3 via changeable microSD card). Various audio files have shown an ability to stimulate treatment points and are readily available. Audio, if chosen, could also acoustically vibrate the needle in a slightly different way, as well as the node under treatment. During trials, the delivery of audio directly to nodes under treatment helped the client relax sooner, and also eased their transition into that deeper state of full relaxation.

Placement needles, at certain points of the body, were generally selected by the acupuncturist using their knowledge of the subject, the clients' target issues, and accepted common practice. The acupuncture needle stimulation unit or pads 14 were applied to any node (see examples, Table 1) chosen for treatment without the need for needles placed at those locations. However, the magnetic permeability of the needle within the field added to the movement of the needle, and enhanced the discrete magnetic fields the acupuncture device 10 delivers. As a general theme, it was notable in most instances that, when using needles within the pads, it appeared that fewer total needles (nodes under treatment) were required to achieve a desired treatment outcome.

TABLE 1

Choice of select acupuncture points used for pad placement.

| Acu Point | Common Name | Location | Goal/Action |
|---|---|---|---|
| Du 2 | Base chakra (Posterior) | Sacro coccygeal hiatus | Lumbar/Legs |
| Du 4 | Lumbar chakra (Posterior) | Space Inferior L2 | Lumbar/Kidney |
| Du 7 | Solar Plexus (Posterior) | Inferior T10/Inferior T9 | Digestive/Liver |
| Du 8 | Solar Plexus (Posterior) | Inferior T10/Inferior T9 | Digestive/Liver |
| Du 11 | Heart Chakra (Posterior) | Inferior T5 | Heart/Pericardium/ Calm |
| Du 12 | Throat Chakra (Posterior) | Inferior T3/ Inferior T1 | Clear Lung/Calm |
| Du 13 | Throat Chakra (Posterior) | Inferior T3/ Inferior T1 | Clear Lung/Calm |
| Pericardium 6 | Motion Sickness/ Nausea Pt | 2.5 finger widths from the palmar wrist crease midpoint | Calms spirit/ Unbinds Chest |
| Kidney 1 | Foot (Minor) Chakra | Sole of foot, between 2nd and 3rd metatarsals | Calm spirit/ Descends excess from the head |
| Yintang | Third Eye | Midpoint of medial extremities of the eyebrows | Calms shen (mind)/ Pacifies wind |
| Ren 21 | Throat Chakra (Anterior) | Midline of sternum just above first intercostal space | Descends lung qi/ benefits throat |
| Ren 17 | Heart Chakra (Anterior) | Midline of sternum level with 4th intercostal space | Unbind the Chest |
| Ren 14 | Solar Plexus (Anterior) | 8 finger widths above navel | Calm spirit/Transform phlegm |

TABLE 1-continued

Choice of select acupuncture points used for pad placement.

| Acu Point | Common Name | Location | Goal/Action |
|---|---|---|---|
| Ren 6 | Lumbar Chakra (Anterior) | 2 finger widths below navel | Tonify qi (energy) |
| Ren 2 | Base Chakra (Anterior) | Superior border pubic symphesis | Warm/invigorate kidneys |

Table 2 provides results from several patients that underwent the acupuncture method in accordance with the present invention. From the patients tested, greater than eighty-five percent of patients (24 of 28) expressed a noticeable shift into greater relaxation quicker. (Sympathetic to Parasympathetic shift). Zero patients expressed any discomfort with the addition of pads to the treatment, during treatment or after treatment. One hundred percent of post treatment clients queried, (20/24 responded). All 20 noted tangibly longer lasting result using the method in accordance with the invention. All long-term clients experiencing the addition of the acupuncture needle stimulation units or pads 14 to their standard treatments reported noticeably improved results (85%), and asked to continue with the treatments in accordance with the invention in future sessions.

TABLE 2

Clinical Trial Patient Demographics & Data

| Patient | Age Tier | Gender | Enhanced Sympathetic to Parasympathetic Shift? | Duration of Effect Greater? |
|---|---|---|---|---|
| Patient 1 | 20's | F | YES | YES |
| Patient 2 | 30's | F | YES | YES |
| Patient 3 | 30's | F | YES | YES |
| Patient 4 | 30's | F | YES | YES |
| Patient 5 | 40's | F | YES | NOT CAPTURED |
| Patient 6 | 40's | F | YES | YES |
| Patient 7 | 40's | F | NO | NO |
| Patient 8 | 40's | F | YES | YES |
| Patient 9 | 40's | F | YES | YES |
| Patient 10 | 40's | F | YES | YES |
| Patient 11 | 40's | F | YES | NOT CAPTURED |
| Patient 12 | 40's | F | YES | YES |
| Patient 13 | 40's | M | YES | YES |
| Patient 14 | 50's | F | YES | YES |
| Patient 15 | 50's | F | NO | NO |
| Patient 16 | 50's | F | YES | YES |
| Patient 17 | 50's | F | YES | YES |
| Patient 18 | 50's | F | YES | YES |
| Patient 19 | 50's | F | YES | YES |
| Patient 20 | 50's | F | YES | NOT CAPTURED |
| Patient 21 | 50's | F | NO | NO |
| Patient 22 | 50's | M | YES | YES |
| Patient 23 | 50's | M | YES | NOT CAPTURED |
| Patient 24 | 60's | F | YES | YES |
| Patient 25 | 60's | F | YES | YES |
| Patient 26 | 70's | M | NO | NO |

Not a single patient observed any overt or incremental adverse effects during or post treatment.

Additional Example: 50 year old female case

Pads were used to deliver a wide range of frequencies to various locations on the body, with each acupuncture needle stimulation unit or pad 14 pair kept in opposition. The acupuncture needle stimulation unit or pads 14 for this case were set at 8 Hz. By design, the acupuncture needle stimulation unit or pads 14 generated a conical-toroidal field that switches poles yet constantly keeps the fields in perfect opposition at the paired pad points that are selected.

Referring to FIG. 20A and FIG. 20B, the general concept of pair placement is shown. The present method may utilize pairs of acupuncture needle stimulation unit or pads 14 placed on the human body 300. In the figures, the acupuncture needle stimulation unit or pad 14 pairs are shown as the following: 1) Superior (S) and Inferior (I): Example Pair A: Du 12 (S) & B: Du (I); 2) Proximal and Distal: Example Pair Y: BL 40 (P) & Z: K1 (D); 3) Local (L) vs Distal (Di): Example Right Shoulder Pain/W: Anterior Deltoid Trigger Point (L) vs. X: LI4 (Di); 4) Extra-Ordinary Vessels: Example K: Yang Wei Confluent Point (TH 5) & Dai Mai Confluent Point L (GB41), and 5) Opposing Points on Right vs Left: Kidney 1 points on both left, keyed Z and right keyed Q. Such examples are illustrative only, as pair placements may be applied as known to one of skill in the art.

The acupuncture needle stimulation unit or pad 14 pairs were observed to effect systemic tension release as well, not just in areas where they are placed. Treatments were administered with or without an acupuncture needle placed at the site through the acupuncture needle stimulation unit or pad 14. Treatments administered without a placed needle are also effective in their own way, delivering a more discrete effect/result, which is often preferred for maintenance treatments.

The 50 year old female presented with chronic asthma, residual neck pain and low lumbar pain resulting from an automotive collision, along with work/family related stress. Some irregularity in sleep (insomnia).

Treatment: pulses reflect 'liver qi constraint'/Sympathetic (adrenal cortex) stimulation with the middle left pulse position as most dominant of six pulses with Wiry pulse overall. Slower/fuller pulse reflects client use of beta-blockers with inhaler. Hollow pulse at the heart/SI point distal left pulse (insomnia reflection).

Three (of four available) pairs of acupuncture needle stimulation unit or pads 14 were placed (using 2 short strips hypo-allergenic double sided tape each pad):

Du Mai 7 at inferior thoracic vertebra 10 paired with Du Mai 2 at the sacrococcygeal hiatus. (Palpation of the paraspinals below the right shoulder blade will be released in myotome-dermatome influence of the Du Mai 7 placement. Distribution of nerve and lymph to the low back and legs will naturally be opened at Du Mai 2 as the Luo of the Du Mai Extra-Ordinary Vessel).

Du Mai 11 at inferior vertebral border T5 will calm the Shen/balance sleep, while its pair at Du Mai 4 at the inferior border of lumbar vertebral border L2, to cool the fire of the heart with water of the kidney.

When using needles, typically 18-gauge needles were placed in the center of each acupuncture needle stimulation unit or pad 14, then using a fortifying needle technique on Du2 and Du 4, and a releasing technique on the remainder. Fortifying technique draws the energy/effect in "deficient" meridians/areas. Releasing technique disperses energy/congestion from "excess" meridians. Deficient and excess are terms in common usage in Acupuncture/Chinese Medicine.

For this patient, needles were placed at trigger/ah-shi points in the upper trapezius, infraspinatus, and supraspinatus bilaterally. The higher gluteals and lateral piriformis demonstrated trigger points as well on palpation and are needled.

Anterior points on the body included settings during treatments: Ren Mai 2: 432 Hz; Ren Mai 4: 480 Hz; Ren 14: 528 Hz; Ren 17: 594 Hz; Ren 21: 672 Hz; YinTang Extra Point: 720 Hz; Du20: 768 Hz. The settings are typically cycled up from the 432 Hz upward to each point, and at treatment end, descend to 432 Hz. This is a centering, energizing type of treatment.

Applying additional stimuli, auditory and visual, directly to the treatment sites:

The acupuncture device 10 was configured to play a stereo sound file which was split and delivered to the acupuncture needle stimulation units or pads 14, where that signal was then converted into sound, which added to as well as aided the treatment acoustically vibrating the needle/ point. The paired acupuncture needle stimulation units or pads 14 each delivered one half of the stereo signal sound output. To stimulate the points under treatment in this case, a specific 7-minute repeating stereo sound file was delivered to acupuncture needle stimulation units or pad 14 sets. The specific sound files chosen, when applied at sites under treatment, cycled up and stimulated their resonant chords for all 7 of the major energy centers.

The treatment acupuncture needle stimulation units or pads 14 also generated and delivered a variety of visible and non-visible light effects. In this case, a synchronous routine of LED light patterns cycles in the following sequence: Looking down at the top of the pad, colors appear in a clockwise sequence throughout the visible range, then pulse in sequence through a range of blue, yellow, orange, red, and green.

As described above, the acupuncture device 10 may use several types of uniquely shaped or designed magnetic coils that may offer advantages over standard magnetic coils, such as but not limited to less electrical resistance, or a boost of the coil's efficiency that also reduces the required current to generate comparable magnetic fields. While the magnetic coils described herein have been described for use in or associated with the acupuncture device 10, any of the magnetic coils described may be used outside of, independently of, or for other applications than the acupuncture device 10.

Figure 21A:
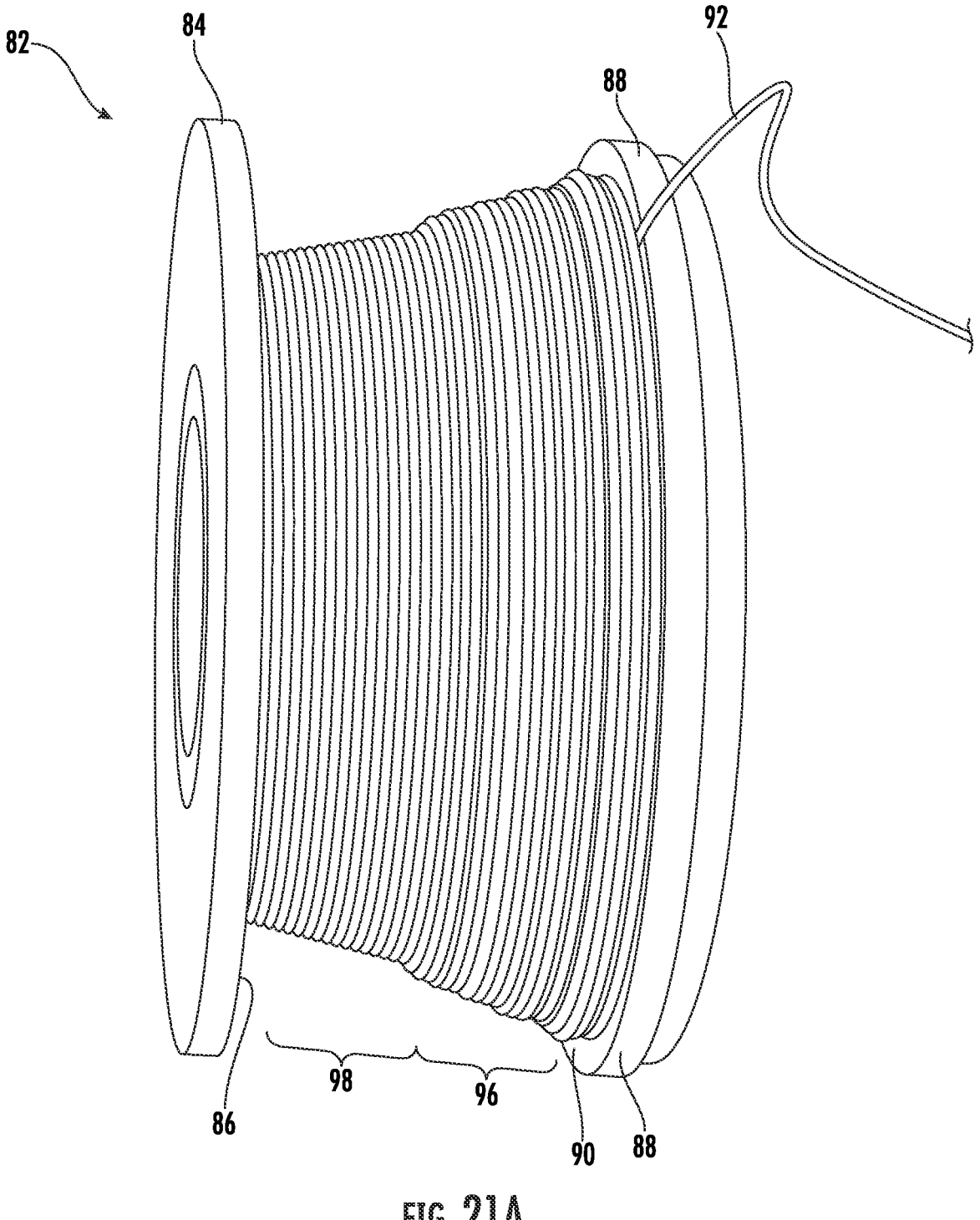
FIG. 21A illustrates a magnetic generator having a coil or wire with individual windings wound around a cylindrical coil core/form in an uneven manner at one end or direction.
Figure 21B:
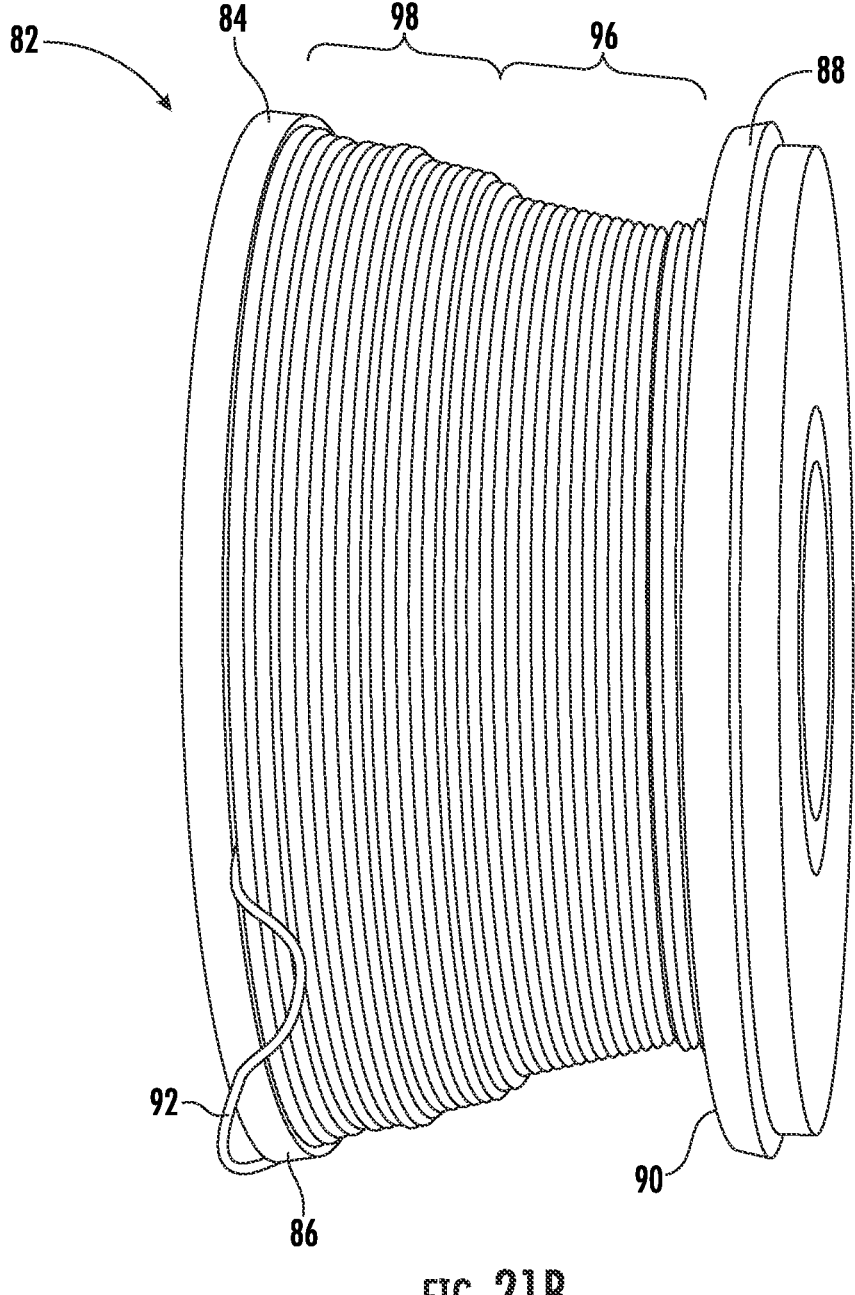
FIG. 21B illustrates a magnetic generator having a coil or wire with individual windings wound around a cylindrical coil core/form in an uneven manner at an end which is opposite than that shown in FIG. 21A.

Referring to FIG. 21A, an illustrative example of a magnetic generator having individual windings (usually a single continuous winding of wire) wound around a cylindrical coil core/forming an uneven fashion, with the majority of its windings located at one end of the core/form is shown. The electromagnetic conical magnetic field generator 82 includes a first disc 84 positioned at or near a first end 86, and a second disc 88, positioned at or near a second end 90. The electromagnetic conical magnetic field generator 82 includes a coil or wire 92 which is wrapped around a form, in this case a conical shaped body, in an uneven fashion (compared to FIG. 13, shown with even wrappings per side. The majority of the windings are located at one end, first section or portion 96 of the core/form, i.e. the conical shaped body 94, as compared to a second section or portion 98 of the core/form, i.e. the conical shaped body 94. Alternatively, the majority of the windings may be located at the second section or portion 98 of the core/form, i.e. the conical shaped body 94 as compared to the first section or portion 96 of the core/form, i.e. the conical shaped body 94, see FIG. 21B.

Figure 22A:
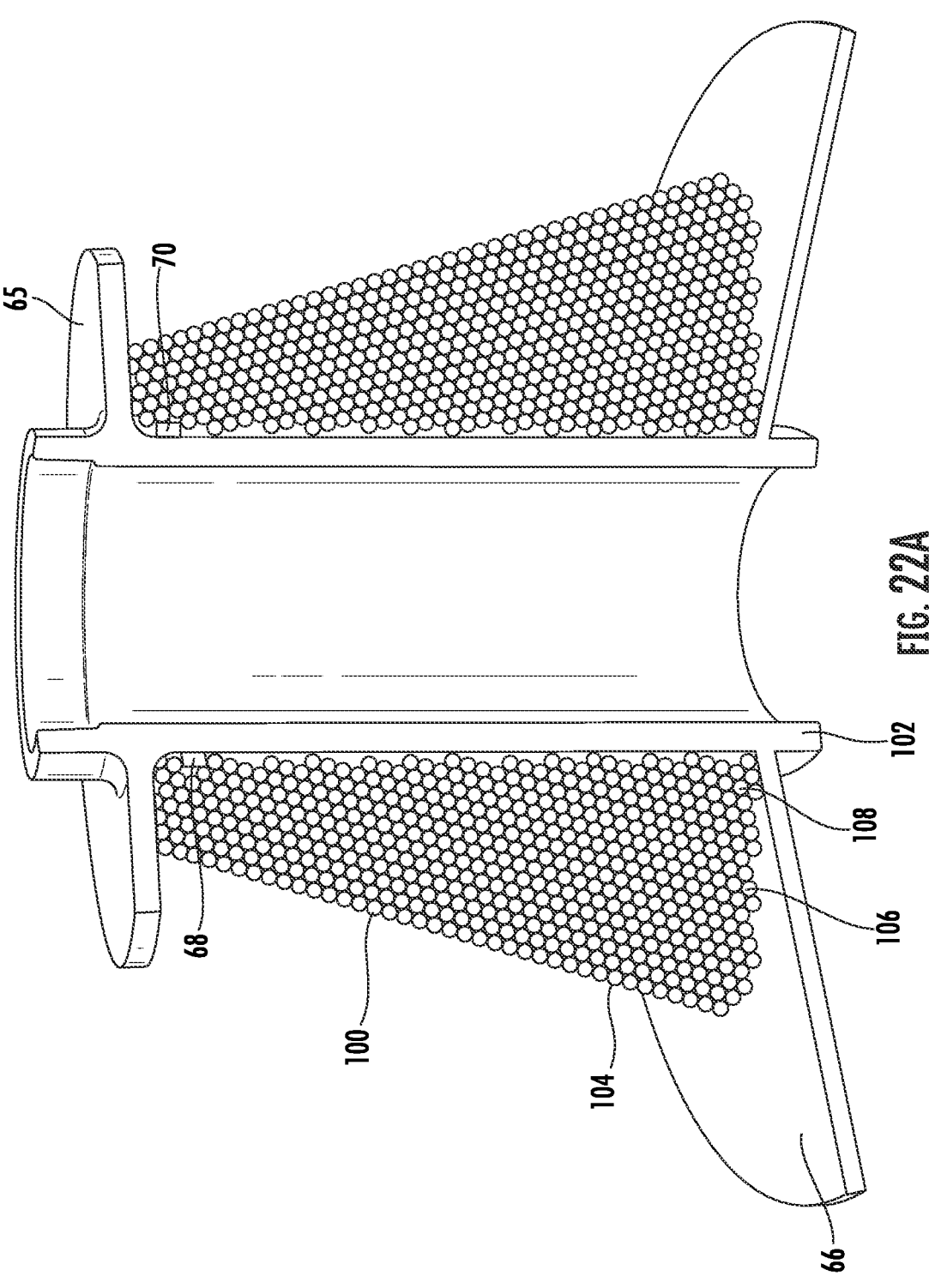
FIG. 22A is a cross section of a magnetic generator having a coil or wire with individual windings wound around a cylindrical coil core/form in an uneven manner, illustrating a conically wound coil with more windings at one end.

FIG. 22A is a cross section of a magnetic generator also showing a coil or wire 100 with individual windings wound around a cylindrical coil core/form 102 in an uneven fashion. The conically wound coil 100 is illustrated with more windings at one side. FIG. 22A also illustrates windings with various lengths, see winding 104 (longest), winding 106 (mid-size, less than winding 104), and winding 108, (smallest, less than mid-size winding 106.

Figure 22B:
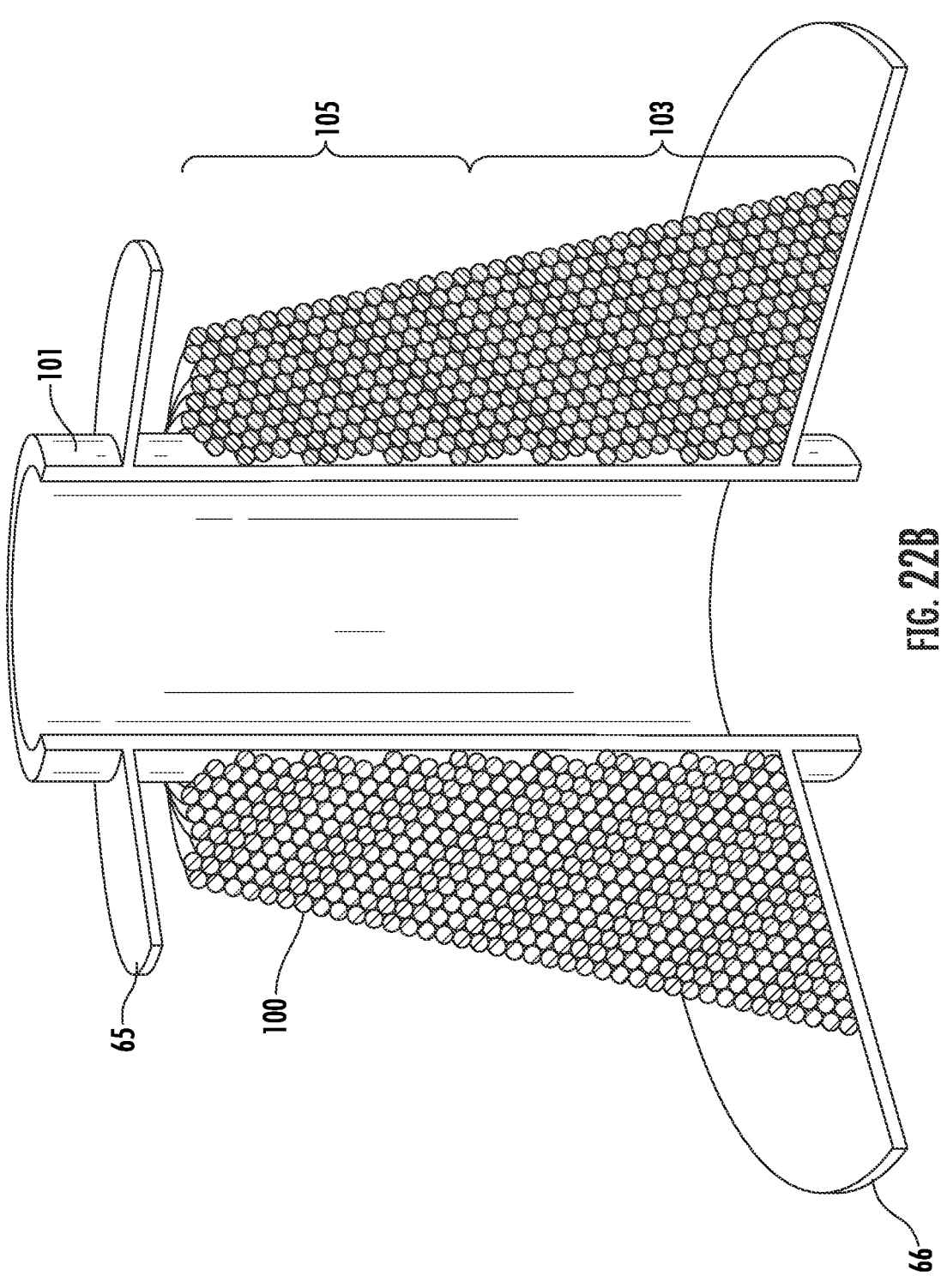
FIG. 22B is a cross section of a magnetic generator having a coil or wire with individual windings wound around a standard core/form in an uneven manner, illustrating a standard coil with more windings at one end.

FIG. 22B is a cross section of the magnetic generator, in standard form, also showing the coil or wire 100 with windings wound around a standard core/form 101 in an uneven fashion. The majority of the coils or wire windings are located at one end, shown as the first section or portion 103 of the core/form (bottom end), as compared to a second end, shown as a second section or portion 105 of the core/form (top end). Alternatively, the majority of coils or wires windings may be located at the second end 105, as compared to the first section or portion 103 of the core/form.

Figure 23A:
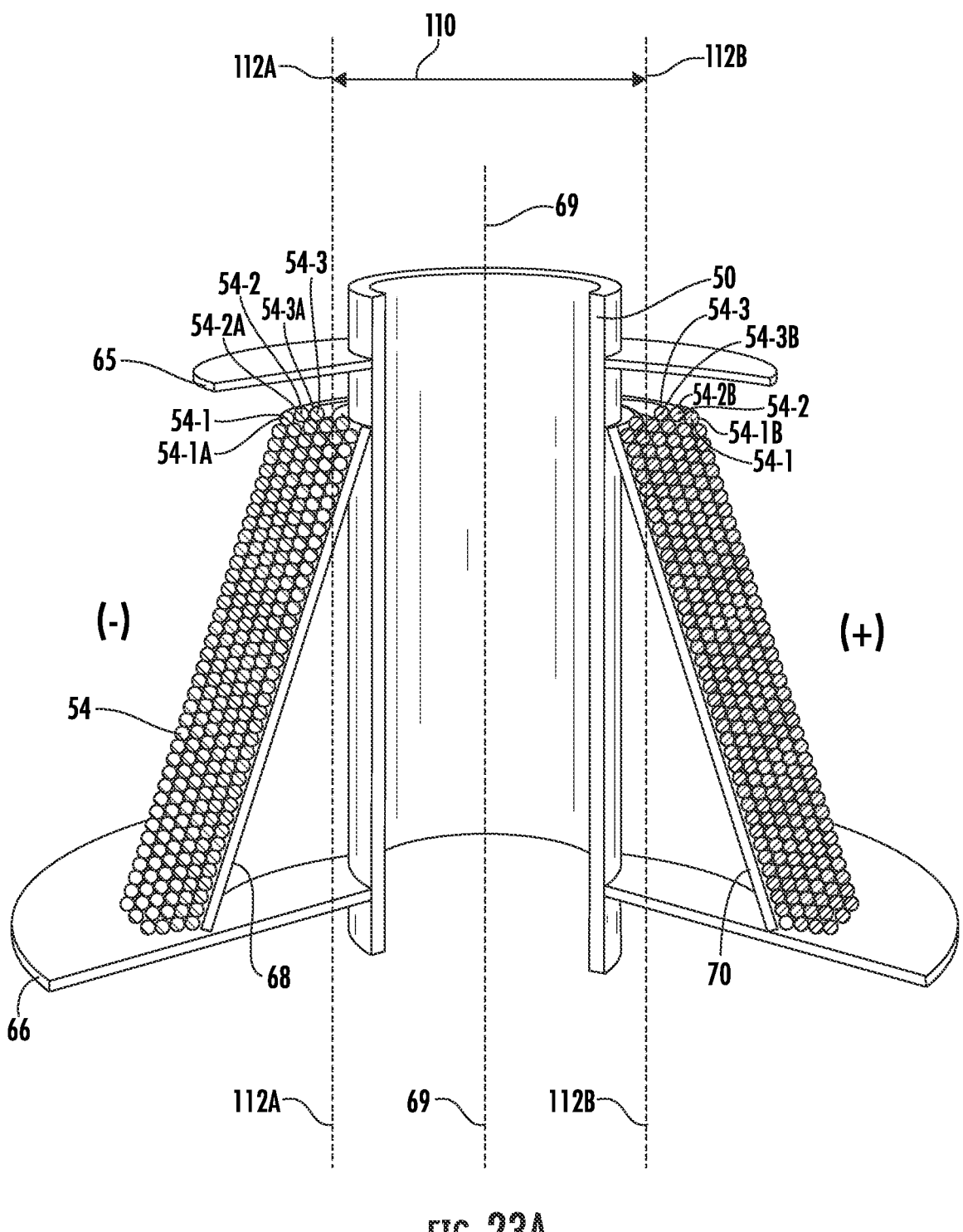
FIG. 23A illustrates a parallel wired, coiled conical magnetic field generator where the magnetic coils or wires are arranged having a connection gap being parallel to a longitudinal axis of a form.
Figure 23B:
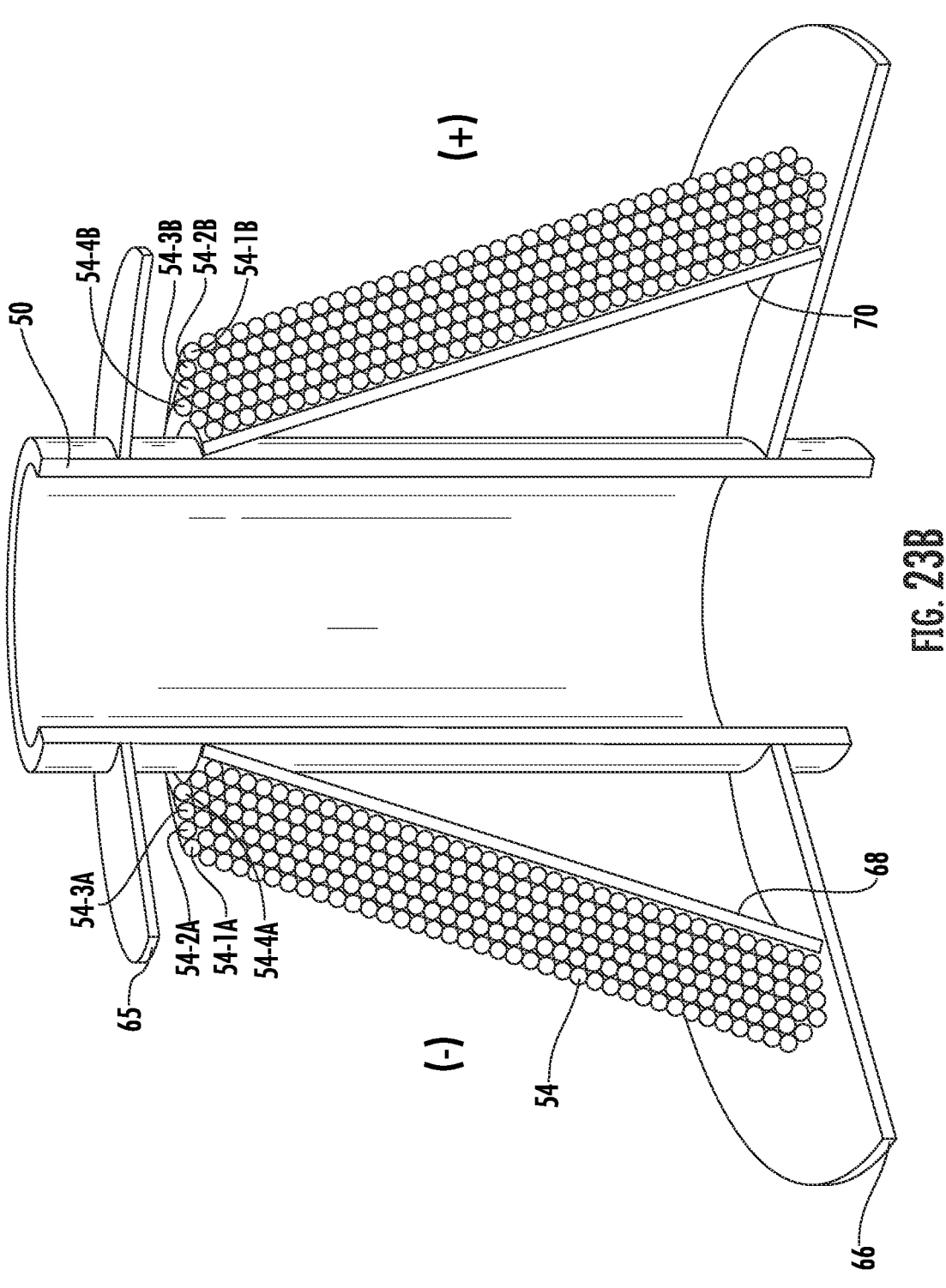
FIG. 23B illustrates the parallel wired connection, with the shaded areas representing wires connected together.
Figure 24:
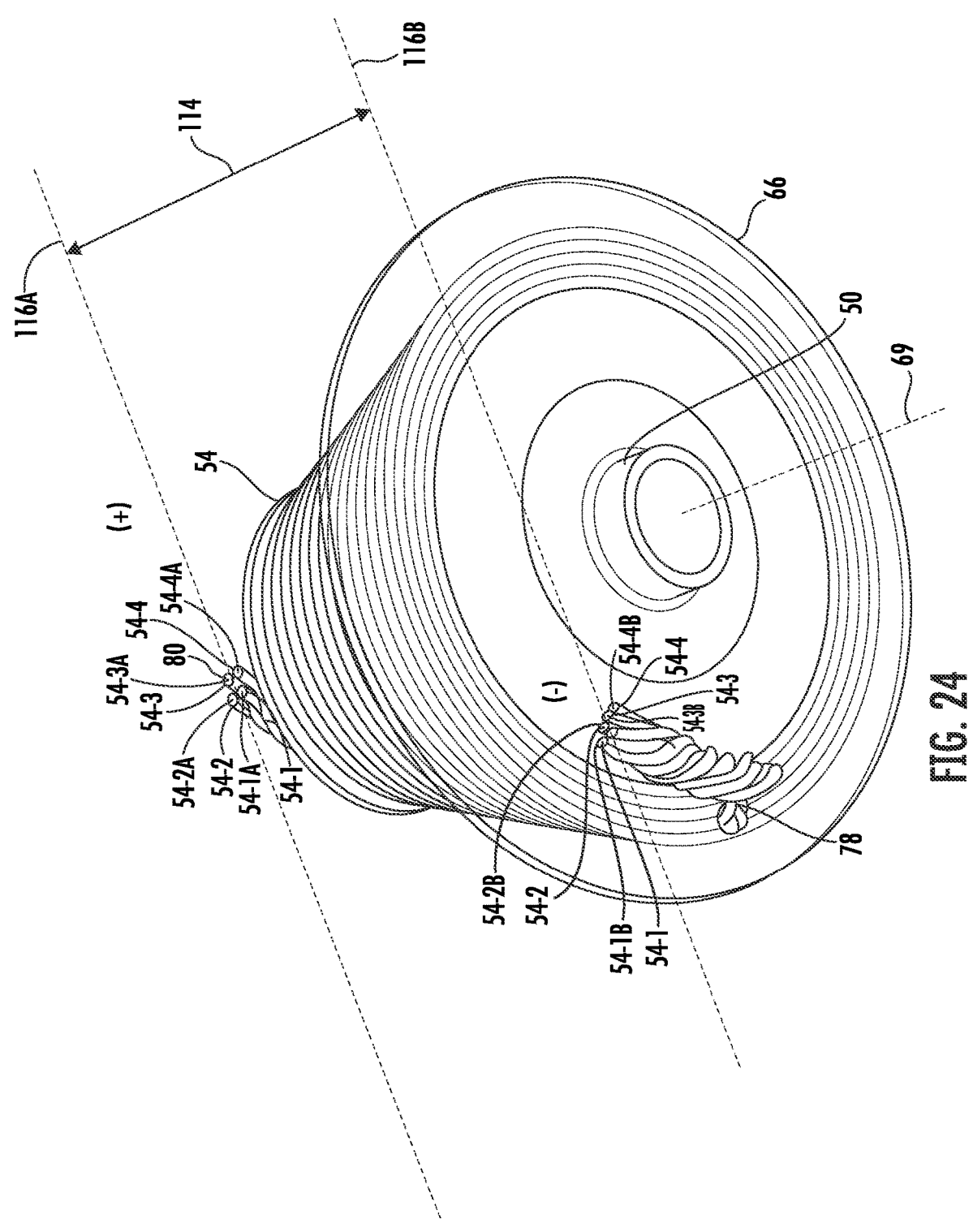
FIG. 24 illustrates a parallel wired, coiled conical magnetic field generator where the magnetic coils or wires are arranged having a connection gap perpendicular to the longitudinal axis of a form.

Referring to FIG. 23A, 23B, and FIG. 24, further descriptions of the parallel wired conical magnetic field generator 76 is provided. The parallel wired conical magnetic field generator 76 comprises magnetic coils or wires 56 that are arranged having a) a connection gap parallel to its core; individual coil windings are wired in a parallel configuration, see FIG. 23A or 23B; or b) with the connection gap perpendicular to its core; each individual not quite a complete wrap (less than a 360 degree complete wrap) is wired in a parallel fashion, see FIG. 24. As used herein, a wind (or winding) of wire is defined as one single strand of wire (coil) which does not complete a circuit or complete a circumference of its core. A winding of wire consists of at least two, preferably any number greater than 2, and more preferably many, single winds of wires which do not complete a circumference of its core and are terminated at each end of their incomplete circumference with those terminations connected so that each of the many windings are wired in a parallel configuration. Accordingly, each individual coil winds around a form in a less than 360 degree manner, i.e. one end or other portion of the coil does not make contact with its opposing end (no portion of the single wire ends up or locates at the same place with any other portion of that single wire), thus forming a gap between each of the coil's ends. Each of the ends of one side, however, are connected together. Such configurations are in contrast to a traditional coiled form in which is designed so that it is made of a long single (one) wrap of that wire wound continuously around a core of any shape or size using the ends of the single wire as input/output connections for the applied energy required.

Referring to FIG. 23A, parallel wired coiled conical magnetic field generator 76 is shown with multiple, individual coils or wires 54 wrapped around form, cylindrical center 50, between the first disc 65 and the second disc 66. Each coil or wire 54 is wraps around the form, cylindrical center 50, in a less than 360-degree manner. Accordingly, individual coil or wire 54-1 has a first end 54-1A that does not connect with a second end 54-1B (thus forming a gap parallel to the longitudinal axis 69 of form/cylindrical center 50). Individual coil or wire 54-2 has a first end 54-2A that does not connect with a second end 54-2B (thus forming a gap parallel to the longitudinal axis 69 of form/cylindrical center 50). Individual coil or wire 54-3 has a first end 54-3A that does not connect with a second end 54-3B (thus forming a gap parallel to the longitudinal axis 69 of form/cylindrical center 50). FIG. 23A illustrates an example of the parallel gap 110, which may be defined by the gap or space between the dashed line 112A (from what would be a first end of wire 54-4) and the dashed line 112B (from what would be the second end of wire 54-4).

The parallel wired coiled conical magnetic field generator 76 may be defined having any number of individual wires or coils, N, where N is at least 2. All ends A, on the left side, are connected (via soldered together or connected via a first hub) together (light shading used to illustrate connected together, see FIG. 23B) and connected to a negative (−) terminal. All ends B, on the right side, are connected (via soldered together or connected via a second hub) together (dark shading used to illustrate connected together, see FIG. 23B) and connected to a positive (+) terminal.

Referring to FIG. 24, the parallel wired coiled conical magnetic field generator 76 comprises magnetic coils or wires 56 that are arranged with the connection gap perpendicular to the longitudinal axis 69 of form/cylindrical core 50; individual coil windings are wired in a perpendicular configuration. The perpendicular gap 114 may be defined by the gap or space between dashed line 116A (from top end of wire 54-1) and dashed line 116B (from the bottom end of wire 54-1). The parallel wired coiled conical magnetic field generator 76 illustrated in FIG. 24 may be defined having any number of individual wires or coils, N, where N is at least 2. Each individual single wire, only four shown, 54-1, 54-2, 54-3, and 54-4, includes a first end 54-1A and second end 54-1B, first end 54-2A and second end 54-2B, first end 54-3A and second end 54-3B, and first end 54-4A and second end 54-4B, connected in parallel. In this arrangement, all first ends A are connected together (and connected to a terminal, i.e. a negative (−) terminal) and all second ends B are connected together (and connected to opposite terminal, i.e. a positive (+) terminal).

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures, and techniques described herein are presently representative of the preferred embodiments, are intended to be exemplary, and are not intended as limitations on the scope.

Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A magnetic coil comprising:
a number of successive wraps wound around a form, each wrap comprising individual wires defined by a first end and a second, opposing, end, wherein some of said individual wires of said successive wraps are of various lengths,
each of said individual wires being wound around said form in a less than complete distance wherein said first end does not make contact with its said second, opposing end, thus forming a connection gap between each of said individual wire's ends, said successive wraps are wired in a parallel configuration wherein each of said individual wire first ends are electrically coupled together and each of said individual wire second ends are electrically coupled together.

2. The magnetic coil according to claim 1, wherein said connection gap is perpendicular to a longitudinal axis of said form.

3. The magnetic coil according to claim 1, wherein said connection gap is parallel to a longitudinal axis of said form.

4. The magnetic coil according to claim 1, wherein said form is a geometrical shape.

5. The magnetic coil according to claim 4, wherein said geometrical shape is a conical shape or cylindrical shape.

6. The magnetic coil according to claim 1, wherein said individual wires are wound around said form between a first member positioned at or near a first end of said form and a second member positioned at or near a second end of said form.

7. The magnetic coil according to claim 1, wherein said individual wires are wound around a pair of angled side walls.

8. The magnetic coil according to claim 1, wherein said individual wires connected at said first end are connected to a negative (−) terminal and said individual wires connected at said second end are connected to a positive (+) terminal.

9. The magnetic coil according to claim 1, wherein said individual wires connected at said first end are connected to a positive (+) terminal and said individual wires connected at said second end are connected to a negative (−) terminal.

* * * * *